United States Patent [19]
Ducep et al.

[11] Patent Number: 5,504,078
[45] Date of Patent: Apr. 2, 1996

[54] α-GLUCOSIDASE INHIBITORS

[75] Inventors: Jean-Bernard Ducep, Sundhoffen; Charles Danzin, Strasbourg, both of France

[73] Assignee: Merrell Dow Pharmaceuticals Inc., Cincinnati, Ohio

[21] Appl. No.: 960,437

[22] PCT Filed: May 17, 1991

[86] PCT No.: PCT/US91/03474

§ 371 Date: Dec. 7, 1992

§ 102(e) Date: Dec. 7, 1992

[87] PCT Pub. No.: WO91/18915

PCT Pub. Date: Dec. 12, 1991

[30] Foreign Application Priority Data

Jun. 8, 1990 [EP] European Pat. Off. ............. 90401582

[51] Int. Cl.$^6$ .................. A61K 31/445; C07H 15/00
[52] U.S. Cl. .............. 514/43; 546/207; 536/17.3
[58] Field of Search ............. 536/17.3; 546/207; 514/43

[56] References Cited

U.S. PATENT DOCUMENTS

| | | |
|---|---|---|
| 4,182,767 | 1/1980 | Murai et al. . |
| 4,220,782 | 9/1980 | Stoltefuss . |
| 4,260,622 | 4/1981 | Junge et al. . |
| 4,405,714 | 9/1983 | Kinast et al. . |
| 4,639,436 | 1/1987 | Junge et al. . |
| 4,806,633 | 2/1989 | Ezure et al. . |
| 5,051,407 | 9/1991 | Böshagen et al. . |
| 5,097,023 | 3/1992 | Ducep et al. . |
| 5,157,116 | 10/1992 | Ducep et al. . |

FOREIGN PATENT DOCUMENTS

| | | |
|---|---|---|
| 0186103 | 7/1986 | European Pat. Off. . |
| 0262404 | 4/1988 | European Pat. Off. . |
| 0315017 | 5/1989 | European Pat. Off. . |
| 3712799 | 10/1987 | Germany . |
| 61-115093 | 6/1986 | Japan . |
| 2064527 | 6/1981 | United Kingdom . |
| 2088365 | 6/1982 | United Kingdom . |
| 2181729 | 4/1987 | United Kingdom . |

OTHER PUBLICATIONS

Chemical Abstracts 90:151998r (May 7, 1979, No. 19) N–Alkylpiperidines. Murai, H. et al. (Nippon Shinyaku Co., Ltd.).

Chemical Abstracts 92:147138j(Apr. 28, 1980; No. 17) Moranoline Derivatives. Matsumura, S. et al.(Nippon Shinyaku Co., Ltd.).

Chemical Abstracts 94:65995p(Mar. 2, 1981, No. 9) N–substituted Moranoline Derivatives. (Nippon Shinyaku Co., Ltd.).

Chemical Abstracts 94:209153n (Jun. 22, 1981, No. 25) 1–2,4–Alkadienyl)–2–hydroxymethyl–3,4,5–trihydroxypiperidines and their use as medicaments. Junge, B. et al. (Bayer AG).

Chemical Abstracts 95:163893u(Nov. 9, 1981, No. 19) Plant Growth Regulators. (Nippon Shinyaku Co., Ltd.).

Chemical Abstracts 96:117597y (Apr. 12, 1982, No. 15) Herbicidal Composition Containing Peperidine Derivatives. Berg, D. et al. (Bayer AG).

Chemical Abstracts vol. 96:163114m (May 10, 1982, No. 19) Cinnamoyl Moranoline Derivatives. Matsumura, S. et al. (Nippon Shinyaku Co., Ltd.).

Chemical Abstracts vol. 97:163420d (Nov. 8, 1982, No. 19) Quaternary ammonium–substituted N–cinnamylpiperidines. Matsumura, S. et al. (Nippon Shinyaku Co., Ltd.).

Chemical Abstracts vol. 106:84991s Glucosylmoranolines. Kawamata, M. et al. (Nippon Shinyaku Co., Ltd.) 1981.

FEBS Letters vol. 237, Nos. 1,2, FEB 06251, 128–132 (Sep. 12, 1988) Inhibition of HIV Replication by Amino–sugar Derivatives. Fleet, G. et al.

Tetahedron vol. 42, No. 20, 5685–5692 (Jul. 29, 1988) The Synthesis from D–xylose of the Potent and Specific nantiomeric Glucosidase Inhibitors, 1,4–Dideoxy–1,4–imino––D–arabinitol and 1,4–dideoxy–1,4–imino–L–arabinitol. Fleet, G. etal.

*Primary Examiner*—Gary Geist
*Assistant Examiner*—Catherine Kilby Scalzo
*Attorney, Agent, or Firm*—Carolyn D. Moon

[57] ABSTRACT

This invention relates to novel polyglycosidyl derivatives of 1-deoxy-nojirimycin, to the processes for their preparation and to their end-use applications, particularly as to their use in the treatment of diabetes.

9 Claims, No Drawings

α-GLUCOSIDASE INHIBITORS

This invention relates to novel polyglycosidyl derivatives of 1-deoxy-nojirimycin, to the processes for their preparation and to their end-use applications, particularly as to their use in the treatment of diabetes.

More specifically this invention relates to novel polyglycosyl derivatives of 1-deoxy-nojirimycin, to the chemical processes for their preparation, to their α-glucosidase inhibiting properties, and to their end-use application in the treatment of diabetes, obesity and those diseases associated with retroviruses, particularly the HIV virus reported to be causative of acquired immune deficiency syndrome (AIDS).

UK Patent Application GB 2 088 365 A discloses a bisglucosylmoranoline derivative useful as a remedy for diabetes mellitus.

European Patent Application Number 87112480.6 discloses glucosylmoranoline derivatives useful as a remedy for diabetes.

Still more specifically this invention relates to the novel 1-deoxy nojirimycin derivatives of the formula I

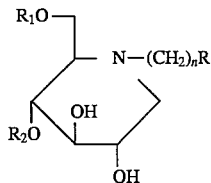

and the pharmaceutically acceptable acid addition salts thereof wherein n is zero, 1 or 2, R is a glycosyl moiety containing 1 to 3 hexose or pentose units, said units optionally bearing an ether or acyl radical at the anomeric carbon atom of the terminal hexose or pentose unit, and one of $R_1$ and $R_2$ is H and the other is α-D-glucopyranosyl. The glycosyl moiety represented by "R" in Formula I are radicals which contain from 1 to 3 hexose or pentose units which optionally bear an ether or an acyl radical at the anomeric carbon atom of the terminal hexose or pentose moiety.

Acid addition salts are those salts forms with such inorganic acids as, for example, hydrochloric, hydrobromic, sulfuric, phosphoric and like acids; with organic carboxylic acids such as, for example, acetic, propionic, glycolic, lactic, pyruvic, malonic, succinic, fumaric, maleic, tartaric, citric, ascorbic, maleic, hydroxymaleic and dihydroxymaleic, benzoic, 2-acetoxybenzoic, mandelic and like acids; and with organic sulfonic acids such as methanesulfonic acid and p-toluenesulfonic acid.

In general, the mono-, di- or trisaccharide moiety (i.e., the glycosyl moiety defined by R) may be attached directly — or thru a $(CH_2)_n$ alkylene bridge — to the nitrogen atom of the 1-deoxynojirimycin moiety thru either an exocyclic or ring carbon atom of the pentose or hexose ring thereby forming a variety of position isomers for each individual glycosyl moiety. Also, similar or dissimilar pentose or hexose moieties may be linked to each other thru a glycosidic oxygen bridge wherein the bridging oxygen atom is attached to an exocylic and/or endocyclic carbon atom of the pentose or hexose moiety of which the glycosyl radical is comprised; again the position isomers all being contemplated as being within the scope of this invention.

Exemplary of glycosyl radicals contemplated by the "R" designation in Formula I are such monosaccharides as 6- or 4-glucosyl, 6- or 4-galactosyl, 4-fucosyl, 1-, 2- or 6-fructosyl, 6- or 4-mannosyl, 4-ribosyl, 4-arabinosyl, 4-xylosyl, 6- or 4-allosyl, 6- or 4-altrosyl, 6- or 4-gulosyl, 6- or 4-idosyl, 6- or 4-talosyl and 4-1-yxosyl, such disaccharides as 4- or 6-isomaltosyl, 4- or 6-trehalosyl, β4- or 6-cellobiosyl, maltosyl, and such trisaccharides as maltotriosyl and cellotriosyl. Preferred glycosyl radicals are 6- or 4-glucosyl, 1- or 6-fructosyl, 6- or 4-maltosyl and 6- or 4-isomaltosyl. Ether derivatives are those derivatives wherein the hydroxyl group attached to the anomeric carbon atom is etherified and include the $C_{1-8}$ alkyl derivatives, preferably methyl, ethyl, propyl, butyl, pentyl, hexyl, cyclohexyl, cyclohexylmethyl, t-butyl, isobutyl, isopropyl and aromatic derivatives such as phenyl and benzyl and the like. Acyl derivatives, such as those formed at the anomeric carbon atom by reaction of the free hydroxy radical with $C_{1-8}$ alkanoic acids or benzoic acids, are also contemplated even though such acylated moieties may easily be removed from the glycosyl radical. Preferred acyl radicals are those formed with acetic or benzoic acids, although acyl radicals formed from such acids as propionic, n-butyric, isobutyric, n-valeric, hexanoic and phenylacetic acid are contemplated.

The α-D-glucopyranosyl moiety of $R_1$ and $R_2$ has the structural formula

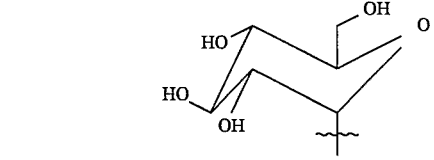

the wavy line indicating the bond by which it is attached to the oxygen of either the 4- or 6- positions of the 1-deoxynojirimycin moiety.

The final products of formula I may be prepared by one of two alternate methods which are depicted by Reaction Scheme A and B. Reaction A involves the condensation of a 1-halo (preferably bromo)-2,3,4-trihydroxy-protected (preferably benzyl)-6-O-t-butyldimethylsilyl-α-D-glucopyranosyl derivative with an N-R'-substituted -2,3,4-trihydroxyprotected (preferably benzyl)-6-O-hydroxyl-1-deoxynojirimycin derivative (R' being an OH-protected glycosyl moiety as previously defined) to produce the expected hydroxy-protected analogs of formula I which are then deprotected to produce the desired compounds embraced by formula I. Reaction Scheme B involves the condensation reaction of a halo derivative of a glycosyl with a 1-deoxynojirimycin bearing an α-D-glucopyranosyl moiety to produce the desired compounds of formula I. In essence, Reaction Scheme A illustrates the preparation of compounds of formula I wherein the α-D-glucopyranosyl moiety is attached to the 1-deoxynojirimycin moiety via the 6-position linkage (i.e., $R_1$ is α-D-glucopyranosyl and $R_2$ is H), whereas Reaction Scheme B illustrates the preparation of compounds of formula I wherein the α-D-glucopyranosyl moiety is attached to the 1-deoxynojirimycin moiety via the 4-position linkage (i.e., $R_2$ is α-D-glucopyranosyl and $R_1$ is H).

For convenience, and to better teach the preparation of the compounds of this invention, Reaction Schemes A and B depict specific reactants. However it is to be understood that the schemes have general applicability to the various glycosyl moieties (as defined by R on formula I) it being understood to those of ordinary still in the art that the hydroxyl groups of any of the R-glycosyl moieties will be suitably protected and deprotected as indicated for the specific reactants used in the Reaction Schemes shown below.

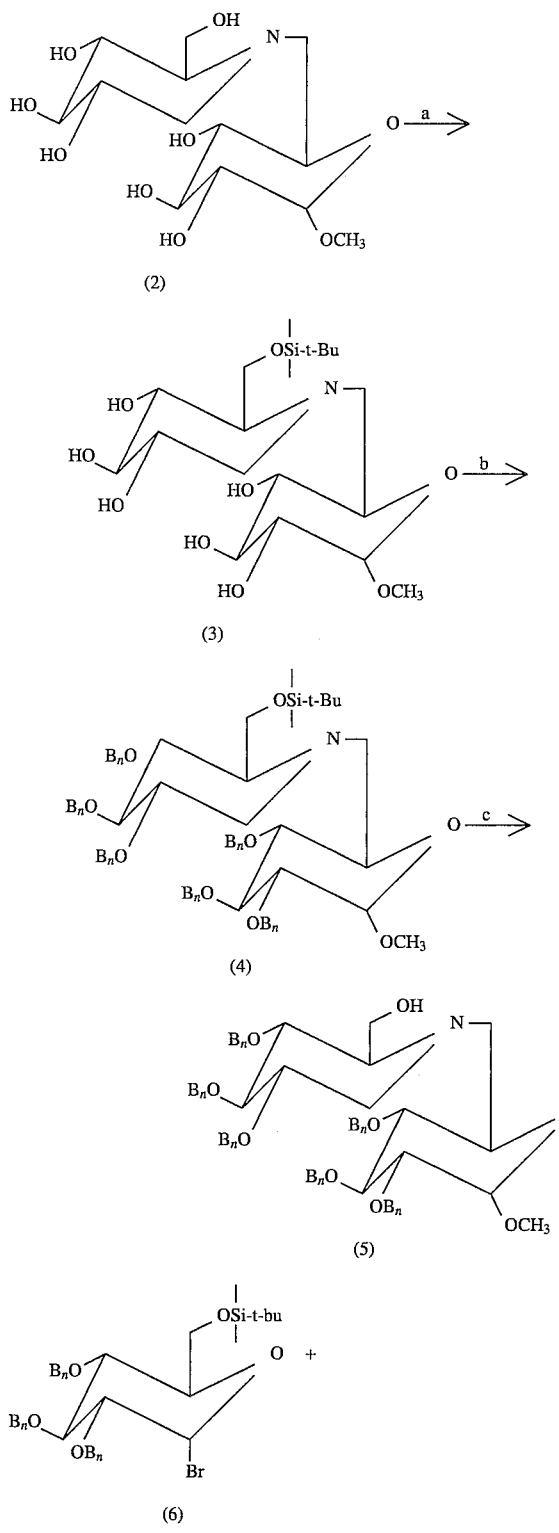
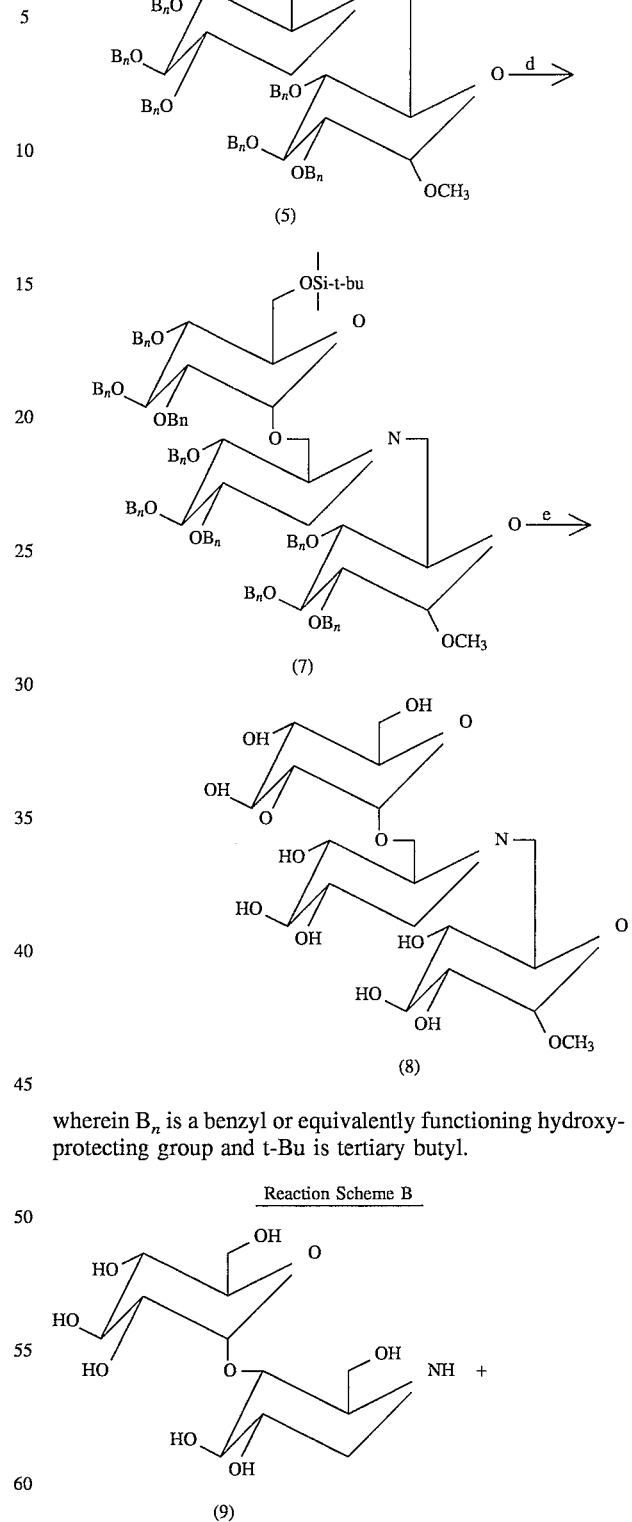
wherein $B_n$ is a benzyl or equivalently functioning hydroxy-protecting group and t-Bu is tertiary butyl.

-continued
Reaction Scheme B

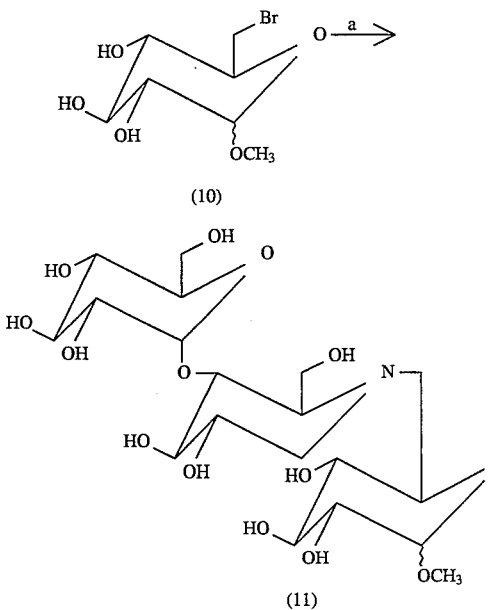

wherein the wavy line of formula 10 and 11 indicates an α- or β-methyl glycoside at the anomeric carbon position (or the α- and β-free hydroxy analog of the glycoside moiety).

In effecting Reaction Scheme A, step (a) entails converting the 6-hydroxy moiety of 1,5-dideoxy-1,5-[(6-deoxy-1-O-methyl-6-α-D-glucopyranosyl)imino] D-glucitol (2) to its O-t-butyldimethylsilyloxy analog (3) by reaction with t-butyldimethylchlorosilane in the presence of imidazole in dimethylformamide. Step (b) converts (3) to its benzylated analogs (4) by reaction with 6 equivalents of benzyl bromide and 6 equivalents of sodium hydride in the presence of n-tetrabutyl ammonium iodide in dimethylformamide at room temperature, preferably overnight and the resulting product hydrolyzed with aqueous ammonium chloride to the desired products which, when subjected to step (c) involving the reaction with n-tetrabutyl ammonium fluoride trihydrate in tetrahydrofuran yields compounds (5). Step (d) involves the reaction of compounds (5) with 2,3,4-tri-O-benzyl-6-O-t-butyldimethylsilyl-α-D-glucopyranosyl bromide (compounds 6) in the presence of diisopropylethylamine in ethanol-free chloroform at room temperature to produce compounds (7) which are then deprotected by standard debenzylation techniques such as catalytic hydrogenation in ethanol using palladium on carbon until up take of hydrogen is complete (about 7 days) or by transfer hydrogenation using formic acid in methanol with Pd/C. When transfer hydrogenation techniques are utilized the products are in the form of their ammonium salts and must be neutralized, preferably using ion exchange resins, such as Dowex AG 1X8 OH⊖form.

In effecting Reaction Scheme B, the 1-deoxy nojirimycin derivative (9) is reacted with the appropriate bromo derivative of an R-glycosyl moiety, e.g. compound (10), in dimethylformamide at about 80° C. for about 48 hours to produce the desired compounds (11).

In general the starting materials such as compounds (2) are known compounds. In those instances wherein the 1-deoxy nojirimycin reactants analogous to compounds of formulae 2,3,4 and 5 which contain a N-glycosyl moiety (i.e. R is glycosyl) other than that shown in formulae 2, 3, 4, 5, 7, 8, 10 and 11, such compounds may also be prepared by methods analogously known in the art. It is preferred to condense an appropriately hydroxy protected 1-deoxynojirimycin (2) with an appropriately hydroxyprotected activated glycosyl moiety, preferably using a trillate or halide, preferably the iodide, but including bromide and chloride and including mesylates or rosylates or other equivalently functioning moieties appreciated by those of ordinary skill in the art. In those instances wherein the 1-deoxy-nojirimycin is coupled with a trillate the reaction is effected by refluxing an admixture of equimolar quantities of the reactants in an alcohol- and water-free solvent, preferably a chlorinated solvent such as chloroform, under an inert atmosphere, preferably under nitrogen or argon, for about 1 to 3 days until the reaction is completed. Following standard procedures for the isolation and purification of the reaction products, the protecting groups are removed to obtain the desired product. Debenzylation is readily effected with standard techniques such as catalytic hydrogenation in an appropriate solvent, e.g. ethanol, using a catalyst such as palladium on carbon, or by transfer hydrogenation using cyclohexene and methanol. In those instances wherein esters were utilized (partially or completely) as the hydroxy protecting groups, it is preferred to first remove the ester group by treatment with an alkali alkoxide, e.g. sodium methoxide, in methanol to hydrolyze the esters and then deprotect the benzyl ethers using the foregoing hydrogenation procedures.

In those instances wherein a glycosyl halide is coupled with the 1-deoxy-nojirimycin the reaction is effected by heating the appropriately hydroxy protected reactants in dry dimethylformamide (DMF) or other equivalently functioning solvent, at about 60°–90° C. for about 12 to 36 hours, said heating taking place using excess amounts of a weak base ($K_2CO_3$) or a molecular sieve, preferably using excess molar amounts of the halide (up to three times) relative to the amine.

The foregoing reactions are illustrated by the following reaction schemes C and D.

Reaction Scheme C

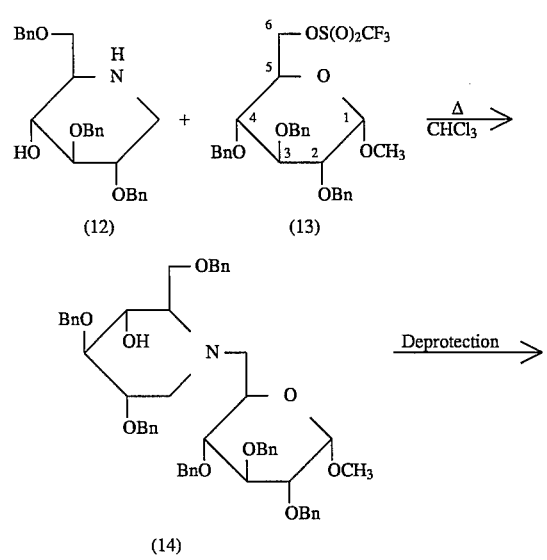

Reaction Scheme C -continued

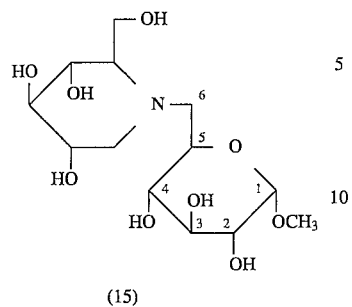

(15)

Reaction Scheme D

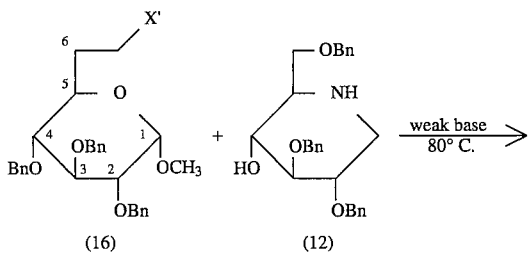

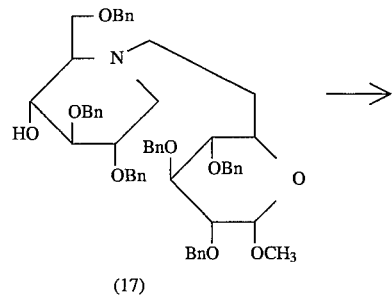

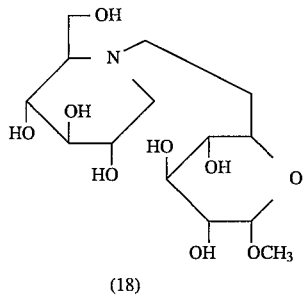

Otherwise depicted, the reaction scheme may more generally be depicted by the following reaction scheme

Reaction Scheme E

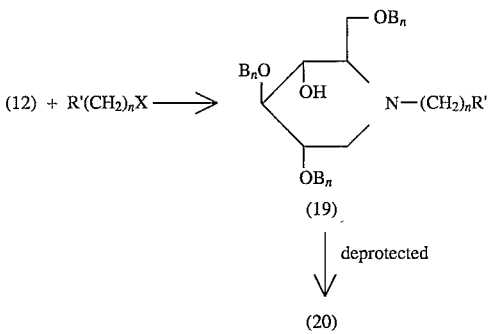

wherein X is a halide (preferably iodide) or a trillate, n is zero, one or two and R' is a glycosyl moiety (as defined by Formula I) having its OH groups protected with a benzyl protecting group, and Bn is benzyl and compound (12) is as depicted in Reaction Schemes C and D.

Appropriately hydroxy protected glycosyl halides (16) and triflates (13) are those glycosyl radicals (mono-, dior trisaccharides of Formula I) where in the hydroxy groups have been protected with an ester or ether moiety. Preferred esters are the acetate or benzoate esters although other alkanoyl esters, particularly those containing up to six carbon atoms, may be used. The preferred ether is the benzyl ether. Such protected compounds may be prepared by standard procedures very well known and understood in the art.

The glycosyl triflates (of which compound 13 is representative) are prepared by standard procedures such as by reaction of an hydroxy protected glycosyl with trifluoromethylsulfonate anhydride in a chlorinated solvent with pyridine for about 1–3 hours at about −78° C. to −10° C. (It is to be noted that the anomeric carbon atom which optionally may be etherified or acylated is that carbon atom at the 1-position of the compound of Formula 13, said carbon atom bearing an ether derivative.)

The glycoside halides (of which compound 16 is representative) may be prepared by standard techniques starting with an appropriately hydroxy protected glycoside bearing one free hydroxy group. In these instances the alcohol is converted to its aldehyde by a Swern oxidation (treatment with oxalyl chloride in dimethylsulfoxide and triethylamine) followed by an insitu conversion of the aldehyde to an olefin by a Wittig reaction (going through a "ylide" prepared from methyltriphenylphosphonium bromide using one equivalent each of n-butyllithium, potassium t-butoxide and t-butanol in tetrahydrofuran at room temperature for about 4 to 8 hours). The olefin is converted to its corresponding alcohol by hydroboration (treatment with borondimethylsulfide, under nitrogen, followed by oxidation with hydrogen peroxide and sodium hydroxide). The alcohol is mesylated (treatment with mesyl chloride in CH$_2$Cl$_2$ in excess NEt$_3$ at −15° C. to 0° C.) and the mesylate converted to its halide (by treatment in ether at 0° C. with magnesium halide), preferably using the iodide.

The 1-deoxy-nojirimycin is prepared by reducing the corresponding δ-lactam of 2,3,6-tribenzyloxy-D-gluconic acid with boron dimethylsulfide followed by treatment with. gaseous hydrochloric acid.

The following examples illustrate the processes and techniques suitable for the preparation of the compounds of this invention.

EXAMPLE 1

Preparation of 1,5-DIDEOXY-4-O-(α,D-GLUCOPYRANOSYL)-1,5-[(6-DEOXY-1-O-METHYL-6-α,D-GLUCOPYRANOSYL)IMINO] -D-GLUCITOL 1,5-Dideoxy-4-O-(α,D-glucopyranosyl)-1,5-imino]-D-glucitol-1,5-dideoxy-4-O-(α,D-glucopyranosyl) -1,5-imino-D-glucitol [Y. Ezure, *Agric. Biol. Chem.*, 49, 2159, ( 1985)] (0.325 g ), 1 mmol ) and methyl 6-bromo-6-deoxy-α-D-glucopyranoside [R. L. Whistler and A. K. M. Anisuzzaman, *Methods Carbohydr. Chem.*, 8, 227, (1980)] (0.282 g, 1.1 mmol) are dissolved in dimethyl formamide (5 ml) and heated during 48 hours at 80° C. Dimethyl formamide is evaporated under high vacuum. The residue is taken with water and neutralized with amberlyst A26 OH$^\ominus$ form (3 g) and filtered. Water is evaporated under vacuum. Flash chromatography on silica gel and elution with a 50:50:4 mixture of methanol, chloroform and water afforded the expected compound 1 ,5-dideoxy-4-O-(α,D-glucopyranosyl)-1,5-[(6-deoxy-1-O-methyl-6-α, D-glucopyranosyl)imino]-D-glucitol as an amorphous sol id (145 mg, 30%).

EXAMPLE 2

Preparation of

6-O-t-BUTYLDIMETHYLSILYL-1,5-DIDEOXY-1,5-[(6-DEOXY-1-O-METHYL-6-α,D-GLUCOPYRANOSYL)IMINO] -D-GLUCITOL 1,5-Dideoxy-1,5-[(6-deoxy-1-O-methyl-6-α,D-glucopyranosyl)-imino]-D-glucitol [European Patent Application EP 0 344 383 A1, published Dec. 6, 1989] (0.5 g, 1.47 mmol) is dissolved in dry dimethyl formamide (5 ml). Imidazole (0.23 g, 3.39 mmol) and t-butyldimethylchlorosilane (0.226 g, 1.5 mmol) are added. The mixture is stirred 48 hours at room temperature. Dimethyl formamide is evaporated under high vacuum. Flash chromatography on silica gel and elution with methanol affords the expected product 6-O-t-butyldimethylsilyl-1,5-dideoxy-1,5-[(6-deoxy-1-O-methyl-6-α, D-glucopyranosyl)-imino] -D-glucitol as an amorphous solid (0.42 g, 63%).

EXAMPLE 3

Preparation of

6-O-t-BUTYLDIMETHYLSILYL-2,3,4-TRI-O-BENZYL-1,5-DIDEOXY-[(2,3,4-TRI-O-BENZYL-6-DEOXY-1-O-METHYL -6-α,D-GLUCOPYRANOSYL)IMINO]-D-GLUCITOL

To a suspension of sodium hydride (0.140 g, 5.84 mmol) in dimethyl formamide (20 ml) are added dropwise 6-O-t-butyldimethylsilyl-1,5-dideoxy-1,5-[(6-deoxy-1 -O-methyl-6-α,D-glucopyranosyl)imino]-D-glucitol (0.42 g, 0.927 mmol), benzyl bromide (1 g, 5.84 mmol) and n-tetrabutyl ammonium iodide (0.221 g, 0.6 mmol) in dimethyl formamide (30 ml). The mixture is stirred overnight and the resulting mixture is hydrolyzed with aqueous ammonium chloride. Dimethyl formamide is evaporated under high vacuum. The residue is taken with water and extracted three times with ethyl acetate. The organic layer is dried over sodium sulfate, filtered and concentrated under reduced pressure. Flash chromatography on silica gel and elution with a 25:75 mixture of ethyl acetate and hexane affords 6-O-t-butyl-dimethylsilyl-2,3-4-tri-O-benzyl-1,5-dideoxy-[(2,3,4 -tri-O-benzyl-6-deoxy-1-O-methyl-6-α,D-glucopyranosyl)imino]-D-glucitol (0.828 g, 90%) as an amorphous solid.

EXAMPLE 4

Preparation of 2,3,4-tri-O-BENZYL-1,5-DIDEOXY-[(2,3,4-TRI-O-BENZYL-6-DEOXY-1-O-METHYL-6-α,D -GLUCOPYRANOSYL)IMINO]-D-GLUCITOL 6-O-t-Butyldimethylsilyl-2,3,4-tri-O-benzyl-1,5-dideoxy-[(2,3,4-tri-O-benzyl-6-deoxy-1-O-methyl-6-α,D-glucopyranosylimino]-D-glucitol (0.82 g, 0.825 mmol) is dissolved in tetrahydrofuran (10 ml) n-tetrabutyl ammonium fluoride trihydrate (0.39 g, 1.24 mmol) is added and the mixture is stirred overnight at room temperature. The solvent is evaporated under reduced pressure. The residue is dissolved in ethyl acetate and washed twice with water. The organic layer is dried over sodium sulfate and concentrated under reduced pressure. Flash chromatography on silica gel and elution with a 1:t mixture of hexane and ethyl acetate affords 2,3,4-tri-O-benzyl-1,5-dideoxy[(2,3,4-tri-O-benzyl-6-deoxy-1-O-methyl-6 -α,D-glucopyranosyl)imino]-D-glucitol as an amorphous solid (0.71 g, 8%).

EXAMPLE 5

Preparation of 1,5-DIDEOXY-2,3,4-TRI-O-BENZYL-6-O-(6-O-TRIMETHYLSILYL-2,3,4-TRI-O-BENZYL-α,D-GLUCOPYRANOSYL-1,5[ (6-DEOXY-2,3,4-TRI-O-BENZYL-1-O-METHYL-6-α,D-GLUCOPYRANOSYL)IMINO]-D-GLUCITOL To a solution of 2,3,4-tri-O-benzyl-6-O-trimethylsilyl-α, D-glucopyranosyl bromide [C. P. Fei and T. H. Chan, *Tetrahedron Letters*, 28, 849, (1987)] (0.43 g, 0.74 mmol) in ethanol-free chloroform ( 3 ml) is added diisopropylethylamine (0.5 ml ) and 2,3, 4-tri-O-benzyl-1,5-dideoxy[(2,3, 4-tri-O-benzyl-6-deoxy -1-O-methyl-6-α,D -glucopyranosyl)-imino]-D-glucitol (0.65 g, 0.74 mmol) in ethanol-free chloroform (3 ml). The mixture is stirred at room temperature during 24 hours. The mixture is diluted with methylene chloride washed with water. The organic layer is dried over sodium sulfate, filtered and concentrated under reduced pressure to afford an amorphous solid. Flash chromatography on silica gel and elution with a 6:4 mixture of hexane and ethyl acetate affords 1,5-dideoxy-2,3,4-tri-O-benzyl-6-O-(6-O-trimethylsilyl-2,3,4-tri-O-benzyl -α,D-glucopyranosyl)-1,5-[(6-deoxy-2,3,4-tri-O-benzyl-1-O- methyl-6-α, D-glucopyranosyl)imino]-D -glucitol as an anomorphous white solid (0.307 g, 30%).

EXAMPLE 6

Preparation of 1,5-DIDEOXY-6-O-(α,D-GLUCOPYRANOSYL)-1,5-[(6-DEOXY-1-O-METHYL-6-α,D-GLUCOPYRANOSYL)IMINO]-D-GLUCITOL 1,5-dideoxy-2,3,4-tri-O-benzyl-6-O-(6-O-trimethylsilyl-2,3,4-tri-O-benzyl-1-O-methyl-6-α,D -glucopyranosyl)-1,5-[(6-deoxy-2,3,4-tri-O-benzyl-1-O-methyl-6-α,D-glucopyranosyl)imino]-D-glucitol (0.3 g, 0.217 mmol) is dissolved in acetic acid (40 ml). Palladium 10% on charcoal (0.6 g) is added. The mixture is hydrogenated during 7 days at 3 atmosphere. The catalyst is removed by filtration and the solvents are evaporated under reduced pressure. The residue is dissolved in water and passed through a column of Amberlyst A26 OH$^\ominus$. Water is evaporated under reduced pressure and flash chromatography on silica gel and elution with a graded mixture of chloroform, methanol and water affords the expected amine 1,5-dideoxy-6-O-(α,D-glucopyranosyl)-1,5-[(6-deoxy-1-O-methyl-6-α,D -glucopyranosyl)imino]-D-glucitol (0.85 g, 79%) as an amorphous solid.

EXAMPLE 7

Preparation of 2,3,6-TRI-O-BENZYL-1,5-DIDEOXY-1,5-IMINO-D-GLUCITOL

To a solution of 2,3,6-tri-O-benzyl-5-deoxy-D-gluconic acid δ-lactam (compound described in Examples 64 to 69) (0.75 g, 1.6 mmol) in dry tetrahydrofuran (15 ml) was added a 10 M solution of borane in methyl sulfide (0.58 ml) under nitrogen at 0° C. The mixture was stirred 15 min at 0° C., 30 min at room temperature, then refluxed during 6 h and finally stirred overnight at room temperature. The mixture was cooled to 0° C. and the excess of borane was destroyed with methanol and stirred 1 h at room temperature. The reaction mixture was treated with gaseous hydrochloric acid and refluxed during 1 h. The solvents were evaporated under reduced pressure. The residue was dissolved in ethyl acetate and washed with a saturated aqueous solution of sodium bicarbonate. The organic layer was dried over sodium sulfate, filtered and concentrated under reduced pressure to afford an oil. Flash chromatography on silica gel and elution with ethyl acetate afforded 2,3,6-tri-O-benzyl-1,5-dideoxy-1,5-imino-D-glucitol which crystallized in methanol (0.655 g, 90%); m.p. 73°–74° C.

EXAMPLE 8

Preparation of

METHYL 2,3,4-TRI-O-BENZYL-6-O-TRIFLUOROMETHYLSULFONYL-α-D-GLUCOPYRANOSIDE

To a solution of dry pyridine (0.46 ml) in methylene chloride (17.5 ml) cooled to −15° C. was added trifluoromethanesulfonic anhydride (0.87 ml). The mixture was stirred during 15 min at −10° C. then methyl 2,3,4-tri-O-benzyl-α-D-glucopyranoside (1.2 g, 2.58 mmol) in methylene chloride (5 ml) was added (P. Kovac, V. Sklenar and C. Glaudemans, *Carbohydr. Res.*, 175, 201 (1988)). The mixture was stirred during 1.5 h at −10° C. The reaction mixture was washed with water. The organic layer was dried over sodium sulfate, filtered and concentrated under reduced pressure to afford an oil. Flash chromatography on silica gel and elution with a 7:3 mixture of hexane and ethyl acetate afforded the expected compound methyl 2,3,4-tri-O-benzyl-6-O-trifluoromethylsulfonyl-α-D-glucopyranoside which was crystallized from hexane (1.43 g, 93%); m.p. 44°–45° C.

EXAMPLE 9

Preparation of 2,3,6-TRI-O-BENZYL-1,5-DIDEOXY-1,5-[(2,3,4-TRI-O-BENZYL-6-DEOXY-1-O-METHYL-6-α-D -GLUCOPYRANOSYL)IMINO]-D-GLUCITOL A solution of methyl 2,3,4-tri-O-benzyl-6-O-trifluoromethylsulfonyl-α-D-glucopyranoside (0.7 g, 1.17 mmol) and 2,3,6-tri-O-benzyl-1,5-dideoxy-1,5-imino-D-glucitol (0.509 g, 1.17 mmol). in ethanol-free chloroform (55 ml) was refluxed under nitrogen during 48 h. The mixture was diluted in methylene chloride and washed successively with a saturated aqueous solution of sodium bicarbonate and saturated brine. The organic layer was dried over sodium sulfate, filtered and concentrated under reduced pressure to afford an oil. Flash chromatography on silica gel and elution with a 6:4 mixture of hexane and ethyl acetate afforded the expected compound 2,3 ,6-tri-O-benzyl-1,5-dideoxy-1,5-[(2,3,4-tri-O-benzyl-6-deoxy-1 -O-methyl-6-α-D-glucopyranosyl)imino]-D-glucitol which was crystallized from methanol (0.772 g, 75%); m.p. 102°–103° C.

EXAMPLE 10

Preparation of 1,5-DIDEOXY-1,5-[(6-DEOXY-1-O-METHYL-6-α-D-GLUCOPYRANOSYL)IMINO]-D-GLUCITOL 2,3,6-tri-O-benzyl-1,5-dideoxy-1,5-[(2,3,4-tri-O-benzyl-6-deoxy-1-O-methyl-6-α-D -glucopyranosyl)imino]-D-glucitol (0.646 g, 0.73 mmol) was dissolved in methanol (20 ml), cyclohexene (10 ml) and Palladium hydroxide 20% on charcoal (1.2 g) were added. The mixture was degased and refluxed 24 h under argon atmosphere. The catalyst was filtered and washed twice with methanol. The solvents were evaporated under reduced pressure. The residue was dissolved in water, the aqueous phase was extracted twice with ethyl acetate. The aqueous layer was put to dryness under reduced pressure to afford a foam. Flash chromatography on silica gel and elution with a 50:50:4 mixture of methanol, chloroform and water afforded the expected compound 1,5-dideoxy-1,5-[(6-deoxy-1-O-methyl-6-α-D-glucopyranosyl)imino]-D-glucitol as a foam (0.13 g, 52%).

EXAMPLE 11

Preparation of

METHYL 2,3,4-TRI-O-BENZYL-6,7-DIDEOXY-α-D-GLUCOHEPT-6-ENOPYRANOSIDE

To a solution of oxalyl chloride (1.05 ml, 17.22 mmol) in dry tetrahydrofuran (40 ml) cooled to −78° C., dry dimethyl sulfoxide (1.3 ml, 18.04 mmol) was added dropwise and then stirred during 35 min at −35° C. The reaction mixture was cooled again to −78° C. and methyl 2,3,4-tri-O-benzyl-α-D-glucopyranoside (6 g, 16.4 mmol) dissolved in tetrahydrofuran (20 ml) was added and the mixture was stirred during 15 min at −35° C., then triethylamine (11.5 ml, 82.65 mmol) was added and the mixture was stirred during 1 h at −35° C. This aldehyde was used without purification and isolation in a Wittig reaction described as follows. To dried triphenylmethylphosphonium bromide (11.7 g, 32.8 mmol) suspended in tetrahydrofuran (700 ml) was added dropwise at −78° C. a 1.42 M solution of n-butyllithium in hexane (23 ml, 32.66 mmol). The reaction mixture was warmed to room temperature and stirred during 1.5 h. Then the mixture was cooled to 0° C. and potassium tertio-butylate (3.68 g, 32.8 mmol) and dry tertio-butyl alcohol (3ml, 31.8 mmol) were added. The mixture was stirred again at room temperature during 30 min. The reaction mixture was cooled to −78° C. and the tetrahydrofuran solution of the aldehyde prepared above was added dropwise. The reaction mixture was warmed to room temperature and stirred during 2 h. A saturated aqueous solution of ammonium chloride and the solvents were evaporated under reduced pressure. The residue was dissolved in ether and washed with water. The organic layer was dried over sodium sulfate, filtered and concentrated under reduced pressure to afford a brown oil. Flash chromatography on silica gel and elution with a 4:96 mixture of ethyl acetate and toluene afforded the expected olefin methyl 2,3,4-tri-O-benzyl-6,7-dideoxy-α-D-glucohept-6-enopyranoside (3.26 g, 55%) which crystallized from hexane; m.p. 46°–47° C.

EXAMPLE 12

Preparation of

METHYL 2,3,4-TRI-O-BENZYL-6-DEOXY-α-D-GLUCOHEPTOPYRANOSIDE

To a solution of methyl 2,3,4-tri-O-benzyl-6,7-dideoxy-α-D-glucohept-6-enopyranoside (0.878 g, 2.43 mmol) in dry tetrahydrofuran (5 ml) was added a 10 M solution of borane in methyl sulfide (0.24 ml, 2.4 mmol) at 0° C. under nitrogen. The mixture was stirred during 3 h at room temperature. The excess of borane was destroyed with ethanol (1 ml). The mixture was cooled at 0° C. 30% hydrogen peroxide (0.3 ml) were added. The mixture was refluxed during 2 h. The reaction mixture was diluted with water and extracted three times with ether. The organic layer was dried over sodium sulfate, filtered and concentrated under reduced pressure to afford an oil. Flash Chromatography on silica gel and elution with a 1:1 mixture of ethyl acetate and hexane afforded the expected alcohol methyl 2,3,4-tri-O-benzyl-6-deoxy-α-D-glucoheptopranoside (0.414 g, 45%) which crystallized from hexane; m.p. 50°–53° C.

EXAMPLE 13

Preparation of

METHYL 2,3,4-TRI-O-BENZYL-6-DEOXY-7-O-METHYLSULFONYL-α-D-GLUCOHEPTOPYRANOSIDE

To a solution of methyl 2,3,4-tri-O-benzyl-6-deoxy-7-O-methylsulfonyl-α-D-glucoheptopyranoside (0.38 g, 0.83 mmol) in dry methylene chloride (10 ml) was added triethylamine (0.2 ml, 1.43 mmol). Then the solution was cooled to −10° C. and mesylchloride (0.08 ml), 1 mmol) was added. The mixture was stirred an additional 15 min at −10° C., then the mixture was allowed to warm up to room temperature. The mixture was washed three times with water. The organic phase was dried over sodium sulfate, filtered and concentrated under reduced pressure to afford a yellow oil. Flash chromatography on silica gel and elution with a 40:60 mixture of ethyl acetate and hexane afforded the expected mesylate methyl 2,3,4-tri-O-benzyl-6-deoxy-7-O-methylsulfonyl-α-D-glucoheptopyranoside as an oil (0.38 g, 91%).

EXAMPLE 14

Preparation of

METHYL 2,3,4-TRI-O-BENZYL-6,7-DIDEOXY-7-IODO-α-D-GLUCOHEPTO-PYRANOSIDE

To a solution of methyl 2,3,4-tri-O-benzyl-6-deoxy-7-O-methylsulfonyl-α-D-glucoheptopyranoside (0.38 g, 0.83 mmol) in ether (5 ml) was added at 0° C. a 0.375 M solution of magnesium iodide (6.7 ml). The mixture was stirred 15 min at 0° C. The excess of magnesium iodide was hydrolyzed with water. The reaction mixture was washed with sodium thiosulfate and Water. The organic layer was dried over sodium sulfate, filtered and concentrated under reduced pressure to afford an oil. Flash chromatography on silica gel and elution with a 2:8 mixture of ethyl acetate and hexane afforded the expected iodide methyl 2,3,4-tri-O-benzyl-6,7-dideoxy-7-iodo-α-D-glucoheptopyranoside which was crystallized from hexane (0.368 g, 91%); m.p. 66°–68° C.

EXAMPLE 15

Preparation of 2,3,6-TRI-O-BENZYL-1,5-DIDEOXY-1,5-[(2,3,4-TRI-O-BENZYL-6,7-DIDEOXY-1-O-METHYL-7-α-D-GLUCOHEPTOPYRANOSYL)IMINO]-D-GLUCITOL A solution of methyl 2,3,4-tri-O-benzyl-6,7-dideoxy-7-iodo-α-D-glucoheptopyranoside (0.338 g, 0.69 mmol) and 2,3,6-tri-O-benzyl-1,5-dideoxy-1,5-imino-D-glucitol (0.1 g, 0.23 mmol) in dry dimethlylformamide (3 ml) was heated at 80° C. overnight along with dry potassium carbonate (0.127 g, 0.92 mmol). The dimethyl formamide was evaporated under reduced pressure. The residue was taken with ethyl acetate and washed twice with water. The organic layer was dried over sodium-sulfate, filtered and concentrated under reduced pressure to afford an oil. Chromatography on neutral aluminum oxide activity III and elution with a 8:2 mixture of hexane and ethyl acetate afforded the expected amine 2,3,6-tri-O-benzyl-1,5-dideoxy-1,5-[(2,3,4-tri-O-benzyl-6,7-dideoxy-1-O-methyl-7-α -D-glucoheptopyranosyl)imino]-D-glucitol which was crystallized in methanol (0.125 g, 60%); m.p. 42°–43° C.

EXAMPLE 16

Preparation of 1,5-DIDEOXY-1,5-[(6,7-DIDEOXY-1-O-METHYL-7-α-D-GLUCOHEPTOPYRANOSYL)IMINO]-D-GLUCITOL 2,3,6-tri-O-benzyl-1,5-dideoxy-1,5-[(2,3,4-tri-O-benzyl-6,7-dideoxyl-1-O-methyl-7-α -D-glucoheptopyranosyl)imino]-D-glucitol (0.1 g, 0.11 mmol) was dissolved in methanol (10 ml) containing ethyl acetate (0.1 ml) and water (1 ml). Palladium hydroxyde 20% on charcoal (0.05 g) was added. The mixture was hydrogenated at 1 atmosphere during two weeks. The catalyst was removed filtration and the solvents were evaporated under reduced pressure. Crystallization of the residue from isopropanol afforded the expected amine 1,5-dideoxy-1,5-[(6,7-dideoxy-1-O-methyl-7-α-D-glucoheptopyranosyl)imino]-D-glucitol (0.023 g, 58%).

EXAMPLE 17

Preparation of 2,3,6-TRI-O-BENZYL-1,5-DIDEOXY-1,5-[(1-DEOXY-2,3:4,5-DI-O-ISOPROPYLIDENE-β-D-FRUCTOPYRANOSYL)IMINO] -D-GLUCITOL A solution of 2,3:4,5-di-O-isopropylidene-1-O-trifluoromethylsulfonyl-8-D-fructopyranose (1.20 g, 3.06 mmol) (P. J. Card and W. D. Hitz, *J. Amer. Chem. Soc.*, 106, 5348 (1984)) and 1,5-dideoxy-2,3,6,-tri-O-benzyl-1,5-imino-D-glucitol (1,331 g, 3.06 mmol) in ethanol-free chloroform (70 ml) is refluxed under nitrogen during 60h. The mixture is diluted with methylene chloride and washed successively with a saturated aqueous solution bicarbonate and saturated brine. The organic layer is dried over sodium sulfate, filtered and concentrated under reduced pressure to afford an oil. Flash chromatography on silica gel and elution with graded mixture of hexane and ethyl acetate will afford the expected amine 2,3,6-tri-O-benzyl-1,5-[(1-deoxy-2,3:4,5-di-O-isopropylidene-β-D -fructopyranosyl)imino]-D-glucitol as an oil.

EXAMPLE 18

Preparation of 2,3,6-TRI-O-BENZYL-1,5-DIDEOXY-1,5-[(1-DEOXY-2-O-METHYL-α-D-FRUCTOFURANOSYL)IMINO-1-D-GLUCITOL 2,3,6-tri-O-benzyl-1,5-dideoxy-1,5-[(1-deoxy-2,3:4,5-di-O-isopropylidene-β-D-fructopyranosyl)imino] -D-glucitol (1.4 g, 2,074 mmol) is dissolved in methanol (100 ml) containing 2% of dry hydrochloric acid. The mixture is refluxed during 48 h. The mixture is neutralized with Amberlyst A 26 OH⁻ form and filtered. The solvents are evaporated under reduced pressure. Flash chromatography on silica gel and elution with graded mixture of ethyl acetate and methanol will afford the expected amine 2,3,6-tri-O-benzyl-1,5-dideoxy-1,5-[(1-deoxy-2-O-methyl-α -D-fructofuranosyl)-imino]-D-glucitol.

EXAMPLE 19

Preparation of 1,5-DIDEOXY-1,5-[(1-DEOXY-2-O-METHYL-α-D-FRUCTOFURANOSYL)IMINO]-D-GLUCITOL The amine 2,3,6-tri-O-benzyl-1,5-dideoxy-1,5-[(1-deoxy-2-O-methyl-α-D-fructofuranosyl)imino]-D-glucitol (0.617 g, 1.014 mmol) is dissolved in methanol (25 ml) containing water (2.5 ml), palladium hydroxide 20% on charcoal (0.3 g) is added. The mixture is hydrogenated during 4 days at atmospheric pressure. The catalyst is removed by filtration and the solvents are evaporated under reduced pressure. Flash chromatography on silica gel and elution with graded mixture of chloroform, methanol and water will afford the expected amine 1,5-dideoxy-1,5-[(deoxy-2-O-methyl-α-D-fructofuranosyl)imino]-D-glucitol as an amorphous solid.

EXAMPLE 20

Preparation of

METHYL 2,3,6-TRI-O-BENZYL-4-O-TRIFLUOROMETHYLSULFONYL-α-D-GALACTOPYRANOSIDE

To a solution of dry pyridine (0.46 ml) in methylene chloride (17.5 ml) cooled to −15° C. is added trifluoromethane sulfonic anhydride (0.87 ml). The mixture is stirred during 15 min at −10° C., then methyl 2,3,6-tri-O-benzyl-α-D-galacto-pyranoside (1.2 g, 2.58 mmol) in methylene chloride (5 ml) is added (N. Morishima, S. Koto, M. Oshima, A. Sugimoto and S. Zen, *Bull. Chem. Soc. Jpn.*, 56, 2849 (1983)). The mixture is washed with water. The organic layer is dried over sodium sulfate, filtered and concentrated under reduced pressure so as to afford an oil which is the expected trillate methyl 2,3,6-tri-O-benzyl-4-O-trifluoromethyl-sulfonyl-α-D-galactopyranoside.

EXAMPLE 21

Preparation of 2,3,6-TRI-O-BENZYL-1,5-DIDEOXY-1,5-[(2,3,6-TRI-O-BENZYL-4-DEOXY-1-O-METHYL-4-α-D -GLUCOPYRANOSYL)IMINO]-D-GLUCITOL A solution of methyl 2,3,6-tri-O-benzyl-4-O-trifluoromethyfulfonyl-α-D-galactopyranoside (1.25 g, 2.53 mmol) and 2,3,6-tri-O-benzyl-1,5-dideoxy-1,5-imino-D-glucitol (1.098 g, 2.53 mmol) in ethanol-free chloroform (70 ml) is refluxed under nitrogen during 3 days. The mixture is diluted with methylene chloride and washed successively with a saturated aqueous solution of sodium bicarbonate and saturated brine. The organic layer is dried over sodium sulfate, filtered and concentrated under reduced pressure so as to afford an oil. Flash chromatography on silica gel and elution with graded mixture of hexane and ethyl acetate will afford the expected amine 2,3,6-tri-O-benzyl-1,5-dideoxy-1,5-[(2, 3,6-tri-O-benzyl-4-deoxy-1-O-methyl -4-α-D-glucopyranosyl)imino]-D-glucitol as an oil.

EXAMPLE 22

Preparation of 1,5-DIDEOXY-1,5-[(4-DEOXY-1-O-METHYL-4-α-D-GLUCOPYRANOSYL)IMINO]-D-GLUCITOL The amine 2,3,6-tri-O-benzyl-1,5-dideoxy-1,5-[(2,3,6-tri-O-benzyl-4-deoxy-1-O-methyl -α-D-glucopyranosyl)imino]-D-glucitol (0.911 g, 1.03 mmol) is dissolved in methanol (20 ml). Cyclohexene (10 ml) and palladium hydroxide 20% on charcoal are added. The mixture is degased and refluxed 16 h under argon atmosphere. The catalyst is filtered and washed twice with methanol. The solvents are evaporated under reduced pressure. The residue is dissolved in water. The aqueous phase is extracted twice with ethyl acetate. The aqueous layer is put to dryness under reduced pressure so as to afford a foam. Flash chromatography on silica gel and elution with a 50:50:4 mixture of methanol, chloroform and water will afford the expected amine 1,5-dideoxy-1,5-[(4-deoxy-1-O-methyl-4-α-D-glucopyranosyl)imino] -D-glucitol as a foam.

EXAMPLE 23

Preparation of

METHYL 2,3,4-TRI-O-BENZYL-6-O-(2,3,4-TRI-O-BENZYL-6-O-TRI-FLUOROMETHYLSULFONYL-α-D-GLUCOPYRANOSYL-α -D-GLUCOPYRANOSIDE

To a solution of dry pyridine (0.24 ml) in methylene chloride (25 ml) cooled to −15° C. is added trifluoromethane sulfonic anhydride (0.45 ml). The mixture is stirred during 15 min at −10° C., then methyl 6-O-(2,3,4-tri-O-benzyl-α-D-glucopyranosyl)-2,3,4-tri-O-benzyl -α-D-glucopyranoside 91.2 g, 1.34 mmol) in methylene chloride (5 ml) is added (R. Eby and C. Schuerch, *Carbohydr. Res.*, 50, 203 (1976)). The mixture is stirred during 1.5 h at −10° C. The reaction mixture is washed with water. The organic layer is dried over sodium sulfate, filtered and concentrated under reduced pressure so as to afford an oil (1.35 g, 98%) which will be the expected trillate methyl-2,3,4-tri-O-benzyl-6-O-(2,3,4-tri-O-benzyl-6 -O-trifluoromethylsulfonyl-α-D-glucopyranosyl)-α-D-glucopyranoside.

EXAMPLE 24

Preparation of 2,3,6-TRI-O-BENZYL-1,5-DIDEOXY-N-[2,3,4-TRI-O-BENZYL-6-DEOXY-1-(2,3,4-TRI-O-BENZYL-1 -O-METHYL-6-O-α-D-GLUCOPYRANOSYL)-α-D-GLUCOPYRANOSYL]-1,5-IMINO-D-GLUCITOL A solution of methyl 2,3,4-tri-O-benzyl-6-O-(2,3,4-O-benzyl-6-O-trifluoromethylsulfonyl-α-D-glucopyranosyl) -α-D-glucopyranoside (1.35 g, 1.31 mmol) and 2,3,6-tri-O-benzyl-1,5-dideoxy-1,5-imino-D-glucitol (0.567 g, 1.31 mmol) in ethanol-free chloroform ( 50 ml ) is refluxed under nitrogen during 48 h. The mixture is diluted with methylene chloride and washed successively with a saturated aqueous solution of sodium bicarbonate and saturated brine. The organic layer is dried over sodium sulfate, filtered and concentrated under reduced pressure so as to afford a foam. Flash chromatography on silica gel and elution with graded mixture of hexane and ethyl acetate will afford the expected amine 2,3,6-tri-O-benzyl-1,5-dideoxy-N-[2,3,4-tri-O-benzyl-6-deoxy-1-(2,3,4-tri-O-benzyl -1-O-benzyl-1-O-methyl-6-O-α-D-glucopyranosyl)-α-D-glucopyranosyl]-1,5-imino-D-glucitol as a foam.

EXAMPLE 25

Preparation of 1,5-DIDEOXY-N-[6-DEOXY-1-(1-O-METHYL-6-O-α-D-GLUCOPYRANOSYL)-α-D-GLUCOPYRANOSYL]-1,5-IMINO-D -GLUCITOL The amine 2,3,6-tri-O-benzyl-1,5-dideoxy-N-[2,3,4-tri-O-benzyl-6-deoxy-1-(2,3,4-tri-O-benzyl-1-O -methyl-6-O-α-D-glucopyranosyl)-α-D-glucopyranosyl]-1,5-imino-D-glucitol (1.2 g, 0.915 mmol) is dissolved in methanol (30 ml). Palladium hydrdxyde 20% on charcoal (0.5 g) is added. The mixture is hydrogenated during 4 days at 3 atmosphere. The catalyst is removed by,filtration and the solvents are evaporated under reduced pressure. Flash chromatography on silica gel and elution with graded mixture of chloroform, methanol and water will afford the expected amine 1,5-dideoxy-N-[6-deoxy-1-(1-O-methyl -6-O-α-D-glucopyranosyl)-α-D-glucopyranosyl]-1,5-imino-D-glucitol as a foam.

EXAMPLE 26

Preparation of

METHYL 6-O-(2,3,4-TRI-O-BENZYL-6,7-DIDEOXY-α-D-GLUCOHEPT-6-ENOPYRANOSYL)-2,3,4-TRI-O-BENZYL-α-D -GLUCOPYRANOSIDE

To a solution of oxalyl chloride (0.37 ml, 5.97 mmol) in dry tetrahydrofuran (40 ml) cooled to −78° C., dry dimethyl sulfoxide (0.45 ml, 6.26 mmol) is added dropwise and then stirred during 35 min at −35° C. The reaction mixture is cooled again to −78° C. and methyl 6-O-(2,3,4-tri-O- -benzyl-α-D-glucopyranosyl)-2,3,4 -tri-O-benzyl-α-D-glucopyranoside (5.1 g, 5.69 mmol) dissolved in tetrahydrofuran (20 ml) is added and the mixture is stirred during 15 min at −35° C., then triethylamine (3.96 ml, 28.45 mmol) is added and the mixture is stirred during 1 h at − 35° C. This aldehyde is to be used without purification and isolation in a Wittig reaction described as follows. To dried triphenylmethylphosphonium bromide (4.059 g, 11.38 mmol) suspended in tetrahydrofuran (100 ml) is added dropwise at −78° C. a 1.55 M solution of n-butyllithium in hexane (7.34 ml, 11.38 mmol). The reaction mixture is warmed to room temperature and stirred during 1.5 h. Then the mixture is cooled to 0° C. and potassium tertio-butylate (1.275 g, 11.38 mmol) and dry tertio-butyl alcohol (1.04 ml, 11.38 mmol) are added. The mixture is stirred again at room temperature during 30 min. The reaction mixture is cooled to −78° C. and the tetrahydrofuran solution of the aldehyde prepared above is added dropwise. The reaction mixture is warmed to room temperature and stirred during 2 h. A saturated aqueous solution of ammonium chloride and the solvents are evaporated under reduced pressure. The residue is dissolved in ethyl acetate and washed with water. The organic layer is dried over sodium sulfate, filtered and concentrated under reduced pressure so as to afford a brown oil. Flash chromatography on silica gel and elution with a graded mixture of carbon tetrachloride and ethyl acetate will afford the expected olefin methyl 6-O-(2,3,4-tri-O-benzyl-6,7-dideoxy-α-D-glucohept-6-enopyranosyl)-2,3,4 -tri-O-benzyl-α-D-glucopyranoside as an amorphous solid.

EXAMPLE 27

Preparation of

METHYL 6-O-(2,3,4-TRI-O-BENZYL-6-DEOXY-α-D-GLUCOHEPTOPYRANOSYL)-2,3,4-TRI-O-BENZYL-α -D-GLUCOPYRANOSIDE

To a solution of methyl 6-O-(2,3,4-tri-O-benzyl-6,7-dideoxy-α-D-glucohept-6-enopyranosyl)-2,3,4 -tri-O-benzyl-α-D-glucopyranoside (2.54 g, 2.85 mmol) in dry tetrahydrofuran (10 ml) is added a 10 M solution of borane in methyl sulfide (0.28 ml, 2.8 mmol) at 0° C. under nitrogen. The mixture is stirred during 3 h at room temperature. Then the mixture is cooled to 0° C. The excess of borane is destroyed with ethanol (1 ml). The mixture is cooled at 0° C. 30% hydrogen peroxide (0.3 ml) and 3 N aqueous solution of sodium hydroxide (0.3 ml) are to be added. The mixture is refluxed during 2 h. The reaction mixture is diluted with water and extracted three times with ethyl acetate. The organic layer is dried over sodium sulfate, filtered and concentrated under reduced pressure so as to afford a foam. Flash chromatography on silica gel and elution with a graded mixture of carbon tetrachloride and ethyl acetate will afford the expected alcohol methyl 6-O-

(2,3,4-tri-O-benzyl-6-deoxy-α-D-glucoheptopyranosyl) -2,3,4-tri-O-benzyl-α-D-glucopyranoside as a foam.

EXAMPLE 28

Preparation of

METHYL 6-O-(2,3,4-TRI-O-BENZYL-6,7-DIDEOXY-7-IODO-α-D-GLUCO-HEPTOPYRANOSYL)-2,3,4-TRI-O-BENZYL-α -D-GLUCOPYRANOSIDE

To a solution of methyl 6-O-(2,3,4-tri-O-benzyl-6-deoxy-α-D-glucoheptopyranosyl)-2,3,4-tri-O-benzyl-α -D-glucopyranoside (1.245 g, 1.37 mmol) in dry methylene chloride (15 ml) is added triethylamine (0.29 ml, 2.05 mmol). Then the solution is cooled to −10° C., and mesylchloride (0.11 ml, 1.42 mmol) is added dropwise. The mixture is stirred an additional 15 min at −10° C., then the reaction mixture is washed three times with water. The organic layer is dried over sodium sulfate, filtered and concentrated under reduced pressure so as to afford a foam which is to be used without further purification. The crude methyl 6-O-(2,3,4-tri-O-benzyl-6-deoxy-7-O-methylsulfonyl-α-D -glucoheptopyranosyl)-2,3,4-tri-O-benzyl-α-D-glucopyranoside is dissolved in ether (20 ml). To this mixture a 0.35 M solution of magnesium iodide in ether (17.5 ml) is added dropwise at 0° C. The excess of magnesium iodide is hydrolyzed with water. The reaction mixture is washed with sodium thiosulfate and water. The organic layer is dried over sodium sulfate, filtered and concentrated under reduced pressure to afford a foam. Flash chromatography on silica gel and elution with a graded mixture of carbon tetrachloride and ethyl acetate will afford the expected iodide methyl 6-O-(2, 3,4-tri-O-benzyl-6,7-dideoxy-7-iodo-α-D -glucoheptopyranosyl)-2,3,4-tri-O-benzyl-α-D-glucopyranoside as a foam.

EXAMPLE 29

Preparation of 2,3,6-TRI-O-BENZYL-1,5-DIDEOXY-N-[-2,3,4-TRI-O-BENZYL-6,7-DIDEOXY-1-(2,3,4-TRI-O-BENZYL-1-O -METHYL-6-O-α-D-GLUCOPYRANOSYL)-7-α-D-GLUCOHEPTOPYRANOSYL]-1,5-IMINO-D-GLUCITOL A solution of the iodide methyl 6-O-(2,3,4-tri-O-benzyl-6,7-dideoxy-7-iodo-α-D-glucoheptopyranosyl)-2,3,4 -tri-O-benzyl-α-D-glucopyranoside (1.145 g, 1.122 mmol) and the amine 2,3,6-tri-O-benzyl- 1,5-dideoxy-1,5-imino-D-glucitol (0.162 g, 0.374 mmol ) in dry dimethylformamide (4 ml) is heated at 80° C. over night along with dry potassium carbonate (0.206 g, 1.49 mmol ). The dimethylformamide is evaporated under reduced pressure. The residue is taken with ethyl acetate and washed twice with water. The organic layer is dried over sodium sulfate, filtered and concentrated under reduced pressure so as to afford a foam. Chromatography on neutral aluminum oxide activity III and elution with a graded mixture of carbon tetrachloride and ethyl acetate will afford the expected amine 2,3,6-tri-O-benzyl-1, 5-dideoxy-N-[2,3,4-tri-O-benzyl-6,7-dideoxy-1 -(2,3,4-tri- O-benzyl-1-O-methyl-6-O-α-D-glucopyranosyl)-7-α-D-glucoheptopyranosyl]-1,5-imino-D-glucitol as a foam.

EXAMPLE 30

Preparation of 1,5-DIDEOXY-N-[6,7-DIDEOXY-1-(1-O-METHYL-6-O-α-D-GLUCOPYRANOSYL)-7-α-D-GLUCOHEPTOPYRANOSYL] -1,5-IMINO-D-GLUCITOL The amine 2,3,6-tri-O-benzyl-1,5-dideoxy-N-[2,3,4-tri-O-benzyl-6,7-dideoxy-1-(2,3,4-tri-O-benzyl -1-O-methyl-6-O-α-D-glucopyranosyl)-α-D-glucoheptopyranosyl]-1,5-imino-D-glucitol (0.337 g, 0.254 mmol) is dissolved in methanol (30 ml). Palladium hydroxide 20% on charcoal (0.4 g) is added. The mixture is hydrogenated during 4 days at 3 atmospheres. The catalyst is removed by filtration and the solvents are evaporated under reduced pressure. Flash chromatography on silica gel and elution with a graded mixture of chloroform, methanol and water will afford the expected amine 1,5-dideoxy-N-[6,7-dideoxy-l-(1-O-methyl-6-O--α-D-glucopyranosyl)-7-α-D -glucoheptopyranosyl]-1, 5-imino-D-glucitol as an amorphous solid.

EXAMPLE 31

Preparation of

METHYL 2,3,6-TRI-O-BENZYL-4-CYANO-4-DEOXY-α-D-GLUCOPYRANOSIDE

A solution of methyl 2,3,6-tri-O-benzyl-4-O-trifluoromethylsulfonyl-α-D-galactopyranoside (3 g, 6.07 mmol) and tetra-n-butyl ammonium cyanide (6.51 g, 24.28 mmol) in ethanol-free chloroform (60 ml) is refluxed under nitrogen during 24 h. The reaction mixture is diluted with methylene chloride, washed twice with water. The organic layer is dried over sodium sulfate, filtered and concentrated under reduced pressure so as to afford an oil. Flash chromatography on silica gel and elution with a graded mixture of hexane and ethyl acetate will afford the expected nitrile methyl 2,3,6-tri-O-benzyl-4-cyano-4-deoxy-α-D-glucopyranoside as an oil.

EXAMPLE 32

Preparation of

METHYL 2,3,6-TRI-O-BENZYL-4-DEOXY-4-FORMYL-α-D-GLUCOPYRANOSIDE

To a solution of methyl 2,3,6-tri-O-benzyl-4-cyano-4-deoxy-α-D-glucopyranoside (1.75 g, 3.7 mmol) in dry tetrahydrofuran (10 ml) is added dropwise at −78° C. a 1.2 M solution of diisobutyl aluminum hydride in n-hexane (3.1 ml). The mixture is stirred under argon at −78° C. during 3 h. Methanol (2 ml) is added and the mixture is warmed to 0° C. Then the solvents are evaporated under reduced pressure. Ether (50 ml) and 0.1 N aqueous hydrochloric acid (40 ml) are added, the mixture is stirred at 0° C. during 1 h. Then after decantation the organic layer is dried over sodium sulfate, filtered and concentrated under reduced pressure so as to afford the expected aldehyde methyl 2,3,6-tri-O-benzyl-4-deoxy-4-formyl-α-D-glucopyranoside as an oil which is used without purification.

EXAMPLE 33

Preparation of

METHYL 2,3,6-TRI-O-BENZYL-4-DEOXY-4-HYDROXYMETHYL-α-D-GLUCO-PYRANOSIDE

The aldehyde methyl 2,3,6-tri-O-benzyl-4-deoxy-4-formyl-α-D-glucopyranoside (1.7 g, 3.57 mmol) is dissolved in ethanol (15 ml). The mixture is cooled to 0° C. and solid sodium borohydride (0.068 g, 1.8 mmol) is added portionwise. The mixture is stirred 1 h at 0° C. Then acetic acid (0.4 ml) is added and the solvents are evaporated under reduced pressure. The residue is taken up with ethyl acetate and washed with saturated aqueous sodium bicarbonate and saturated brine. The organic layer is dried over sodium sulfate, filtered and concentrated under reduced pressure so as to afford an oil. Flash chromatography over silica gel and elution with a graded mixture of hexane and ethyl acetate will afford the expected alcohol methyl 2,3,6-tri-O-benzyl-4-deoxy-4-hydroxy-methyl-α-D-glucopyranoside as an oil.

EXAMPLE 34

Preparation of

METHYL 2,3,6-TRI-O-BENZYL-4-DEOXY-4-TRIFLUOROMETHYL-SULFONYLOXYMETHYL-α-D-GLUCOPYRANOSIDE

To a solution of dry pyridine (0.45 ml) in methylene chloride (30 ml) cooled to −15° C. is added trifluoromethanesulfonic anhydride (0.84 ml). The mixture is stirred during 15 min at −10° C., then methyl 2,3,6-tri-O-benzyl-4-deoxy-4-hydroxymethyl-α-D-glucopyranoside (1.19 g, 2.49 mmol) in methylene chloride (5 ml) is added. The mixture is stirred during 1.5 h at −10° C. The reaction mixture is washed with water. The organic layer is dried over sodium sulfate, filtered and concentrated under reduced pressure so as to afford an oil which is the expected trillate methyl 2,3,6-tri-O-benzyl-4-deoxy-4-trifluoromethylsulfonyloxymethyl-α-D-glucopyranoside.

EXAMPLE 35

Preparation of

2,3,6-TRI-O-BENZYL-1,5-DIDEOXY-1,5-[(2,3,6-TRI-O-BENZYL-4-DEOXY-1-O-METHYL-4-α-D-GLUCOPYRANOSYL)METHYLIMINO]-D-GLUCITOL

A solution of methyl 2,3,6-tri-O-benzyl-4-deoxy-4-trifluoromethylsulfonyloxymethyl-α-D-glucopyranoside (1 g, 1.64 mmol) and 2,3,6-tri-O-benzyl-1,5-dideoxy-1,5-imino-D-glucitol (0.71 g, 1.64 mmol) in ethanol-free chloroform (60 ml) is refluxed under nitrogen during 48 h. The mixture is diluted in methylene chloride and washed successively with a saturated aqueous solution of sodium bicarbonate and saturated brine. The organic layer is dried over sodium sulfate, filtered and concentrated under reduced pressure so as to afford a foam. Flash chromatography on silica gel and elution with a graded mixture of hexane and ethyl acetate will afford the expected amine 2,3,6-tri-O-benzyl-1,5-dideoxy-1,5-[(2,3,6-tri-O-benzyl-4-deoxy-1-O-methyl-4-α-D -glucopyranosyl)-methylimino]-D-glucitol as a foam.

EXAMPLE 36

Preparation of

1,5-DIDEOXY-1,5-[(4-DEOXY-1-O-METHYL-4-α-D-GLUCOPYRANOSYL)METHYLIMINO]-D-GLUCITOL

The amine 2,3,6-tri-O-benzyl-1,5-dideoxy-1,5-[(2,3,6-tri-O-benzyl-4-deoxy-1-O-methyl-4-α-D -glucopyranosyl)methylimino]-D-glucitol (0.98 g, 1.09 mmol) is dissolved in methanol (20 ml). Cyclohexene (10 ml) and palladium hydroxide 20% on charcoal (0.8 g) are added and the mixture is refluxed under nitrogen during 8 h. The catalyst is removed by filtration and the solvents are evaporated under reduced pressure. Flash chromatography on silica gel and elution with a graded mixture of chloroform, methanol and water will afford the expected amine 1,5-dideoxy-1,5-[(4-deoxy-1-O-methyl-4-α-D-glucopyranosyl)methylimino]-D-glucitol as an amorphous solid.

EXAMPLE 37

Preparation of

2,3,6-TRI-O-BENZYL-D-GALACTOPYRANOSE

Methyl 2,3,6-tri-O-benzyl-α-D-galactopyranoside (5 g, 10.775 mmol) is dissolved at 0° C. in a 9:1 mixture of trifluoroacetic acid and water (50 ml) [N. Morishima, S. Koto, M. Oshima, A. Sugimoto and S. Zen, *Bull. Chem. Soc. Jpn.*, 56, 2849 (1983)]. The mixture. is stirred overnight at 0° C. The solvents are evaporated under reduced pressure without heating. The residue is dissolved in ethyl acetate and washed successively with sodium bicarbonate and brine. The organic layer is dried over sodium sulfate, filtered and concentrated under reduced pressure so as to afford an oil. Flash chromatography on silica gel and elution with a graded mixture of ethyl acetate and hexane will afford 2,3,6-tri-O-benzyl-D-galactopyranose as an oil.

EXAMPLE 38

Preparation of

1,4-DI-O-ACETYL-2,3,6-TRI-O-BENZYL-D-GALACTOPYRANOSE 2,3,6-tri-O-benzyl-D-galactopyranose (3.927 g, 8.72 mmol) is dissolved in dry pyridine (25 ml) and acetic anhydride (5 ml) is added. The mixture is stirred during 24 h at room temperature. The solvent is evaporated under high vacuum. The residue is dissolved in ethyl acetate and washed with water. The organic layer is dried over sodium sulfate, filtered and concentrated under reduced pressure so as to afford the expected diacetate 1,4-di-O-acetyl-2,3,6-tri-O-benzyl-D-galactopyranose (4.64 g, 99%) as an oil which can be used without purification.

EXAMPLE 39

Preparation of

4-O-ACETYL-2,3,6-TRI-O-BENZYL-α-D-GALACTOPYRANOSYL CHLORIDE

A solution of 1,4-di-O-acetyl-2,3,6-tri-O-benzyl-D-galactopyranose (4.64 g, 8.67 mmol) in ether (10 ml) is treated with ethereal hydrogen chloride (0.2 g/ml, 25 ml). The mixture is stirred at room temperature during 48 h. The solvents are evaporated under reduced pressure so as to afford an oil. Flash chromatography on silica gel and elution with a graded mixture of carbon tetrachloride and ethyl acetate will afford 4-O-acetyl-2,3,6-tri-O-benzyl-α-D-galactopyranosyl chloride as an oil.

EXAMPLE 40

Preparation of

METHYL 4-O-(4-O-ACETYL-2,3,6-TRI-O-BENZYL-α-D-GALACTOPYRANOSYL)-2,3,6-TRI-O-BENZYL-α-D-GLUCOPYRANOSIDE

Ethereal silver perchlorate (0.08 M, 84.5 ml, 6.76 mmol) is added with stirring at −30° C. to a solution of methyl-2, 3,6-tri-O-benzyl-α-D-glucopyranoside (2.284 g, 4.93 mmol) (P. J. Garegg, H. Hultberg and S. Wallin, *Carbohydr. Res.*, 108, 97 (1982)), 4-O-acetyl-2,3,6-tri-O-benzyl-α-D-galactopyranosyl chloride (3.142 g, 6.154 mmol) and 2,4,6-trimethylpyridine (0.89 ml, 6.76 mmol) in ether (20 ml). The mixture is stirred 15 min at −30° C. and silver chloride precipitated. The mixture is filtered through a celite pad, the solids are washed with ether, the filtrate is concentrated under reduced pressure. The residue is dissolved in methylene chloride and the organic layer is washed successively with aqueous sodium thiosulfate and water. The organic layer is dried over sodium sulfate, filtered and concentrated under reduced pressure so as to afford a foam. Flash chromatography on silica gel and elution with a graded mixture of hexane and ethyl acetate will afford methyl 4-O-(4-O-acetyl-2,3,6-tri-O-benzyl-α-D-galactopyranosyl)-2,3,6-tri-O-benzyl-α-D -glucopyranoside as a foam.

EXAMPLE 41

Preparation of

METHYL 2,3,6-TRI-O-BENZYL-4-O-(2,3,6-TRI-O-BENZYL-α-D-GALACTOPYRANOSYL)-α-D-GLUCOPYRANOSIDE

Methyl 4-O-(4-O-acetyl-2,3,6-tri-O-benzyl-α-D-galactopyranosyl)-2,3,6-tri-O-benzyl-α-D-glucopyranoside (2.543 g, 2.71 mmol) is dissolved in hot toluene (2 0 ml) and methanol (80 ml) is added, followed by a few drops of 1 M methanolic sodium methoxide. The mixture is stirred at room temperature during 2 h. The reaction mixture is made neutral with Amberlite IR 120 (H$^+$) resin, filtered and concentrated under reduced pressure so as to afford methyl 2,3,6-tri-O-benzyl-4-O-(2,3,6-tri-O-benzyl-α-D-galactopyranosyl)-α-D -glucopyranoside as an amorphous solid.

EXAMPLE 42

Preparation of

METHYL 4-O-(2,6-TRI-O-BENZYL-4-O-TRIFLUOROMETHYLSULFONYL-α-D-GALACTOPYRANOSYL)-2,3,6-TRI-O-BENZYL -α-D-GLUCOPYRANOSIDE

To a solution of dry pyridine (0.49 ml) in dry methylene chloride (40 ml) cooled to −15° C. is added trifluoromethane sulfonic anhydride (0.91 ml). The mixture is stirred during 15 min at −10° C., then methyl 2,3,6-tri-O-benzyl-4-O-(2,3,6-tri-O-benzyl-α-D -galactopyranosyl)-α-D-glucopyranoside (2.428 g, 2.71 mmol) in methylene chloride (10 ml) is added. The mixture is stirred during 1.5 h at −10° C. The reaction mixture is washed with water. The organic layer is dried over sodium sulfate, filtered and concentrated under reduced pressure so as to afford an oil which will be the expected triflate methyl 4-O-(2,3,6-tri-O-benzyl-4-O-trifluoromethylsulfonyl-α-D-galactopyranosyl) -2,3,6-tri-O-benzyl-α-D-glucopyranoside.

EXAMPLE 43

Preparation of 2,3,6-TRI-O-BENZYL-1,5-DIDEOXY-N-[2,3,6-TRI-O-BENZYL-4- DEOXY-1-(2,3,6-TRI-O-BENZYL-1-O-METHYL-4-O-α-D-GLUCOPYRANOSYL)-α-D-GLUCOPYRANOSYL]-1-5-IMINO-D-GLUCITOL A solution of methyl 4-O-(2,3,6-tri-O-benzyl-4-O-trifluoromethylsulfonyl-α-D-galactopyranosyl)-2,3,6-tri-O-benzyl -α-D-glucopyranoside (1.52 g, 1.46 mmol) and 2,3,6-tri-O-benzyl-1,5-dideoxy-1,5-imino-D-glucitol (0.632 g, 1.46 mmol) in ethanol-free chloroform (50 ml) is refluxed under nitrogen during 48 h. The mixture is diluted in methylene chloride and washed successively with a saturated aqueous solution of sodium bicarbonate and saturated brine. The organic layer is dried over sodium sulfate, filtered and concentrated under reduced pressure so as to afford a foam. Flash chromatography on silica gel and elution with a graded mixture of hexane and ethyl acetate will afford the expected amine 2,3,6-tri-O-benzyl-1,5-dideoxy-N-[2,3,6-tri-O-benzyl-4-deoxy-1-(2,3,6-tri-O-benzyl -1-O-methyl-4-O-α-D-gluco-pyranosyl)-α-D-glucopyranosyl]-1,5-imino-D-glucitol as an amorphous solid.

EXAMPLE 44

Preparation of 1,5-DIDEOXY-N-[4-DEOXY-1-(1-O-α-METHYL-4-O-α-D-GLUCOPYRANOSYL)-α-D-GLUCOPYRANOSYL]-1,5 -IMINO-D-GLUCITOL 2,3,6-tri-O-benzyl-1,5-dideoxy-N-[2,3,6-tri-O-benzyl-4-deoxy-1-(2,3,6-tri-O-benzyl-1-O-methyl -4-O-α-D-glucopyranosyl)-α-D-glucopyranosyl]-1,5-imino-D-glucitol (1 g, 0.762 mmol) is dissolved in methanol (30 ml). Palladium hydroxide 20% on charcoal (0.5 g) is added. The mixture is hydrogenated during 4 days at 3 atmospheres. The catalyst is removed by filtration and the solvents are evaporated under reduced pressure. Flash chromatography on silica gel and elution with a graded mixture of chloroform, methanol and water will afford the expected amine 1,5-dideoxy-N-[4-deoxy-1-(1-O-methyl-4-O-α-D-glucopyranosyl)-α -D-glucopyranosyl]-1,5-imino-D-glucitol as an amorphous solid.

EXAMPLE 45

Preparation of

1-ETHENYL-1,2:3,4-DI-O-ISOPROPYLIDENE-β-D-ARABINOPYRANOSE

To a solution of oxalyl chloride (1.05 ml, 17.22 mmol) in dry tetrahydrofuran (40 ml) cooled to −78° C., dry dimethyl sulfoxide (1.3 ml, 18.04 mmol) is added dropwise and then stirred during 35 min at −35° C. The reaction mixture is cooled again to −78° C. and 2,3:4,5-di-O-isopropylidene-D-fructopyranose (4.26 g, 16.4 mmol) (R. F. Brady, *Carbohydr. Res.*, 15, 35 (1970)) dissolved in tetrahydrofuran (20 ml) is added and the mixture is stirred during 15 min at −35° C. then triethylamine (11.5 ml, 82.65 mmol) is added and the mixture is stirred during 1 h at −35° C. This aldehyde can be used without purification and isolation in a wittig reaction described as follows. To dried triphenylmethylphosphonium bromide (11.7 g, 32.8 mmol) suspended in tetrahydrofuran (400 ml) is added dropwise at −78° C. a 1.55 M solution of n-butyllithium in hexane (21 ml, 32.66 mmol). The reaction mixture is warmed to room temperature and stirred during 1.5 h. Then the mixture is cooled to 0° C. and potassium tertio-butylate (3.68 g, 32.8 mmol) and dry tertio-butyl alcohol (3 ml, 31.8 mmol) are added. The mixture is stirred again at room temperature during 30 min. The reaction mixture is cooled to −78° C. and the tetrahydrofuran solution of the aldehyde prepared above is added dropwise. The reaction mixture is warmed to room temperature and stirred during 2 h. A saturated aqueous solution of ammonium chloride and the solvents are evaporated under reduced pressure. The residue is dissolved in ether and washed with water. The organic layer is dried over sodium sulfate, filtered and concentrated under reduced pressure so as to afford a brown oil. Flash chromatography on silica gel and elution with a graded mixture of hexane and ethyl acetate will afford the expected olefin 1-ethenyl-1,2,3,4-di-O-isopropylidene-β-D-arabinopyranose as an oil.

EXAMPLE 46

Preparation of 1,2:3,4-DI-O-ISOPROPYLIDENE-1-(2-HYDROXY-ETHYL)-β-D-ARABINOPYRANOSE To a solution of 1-ethenyl-1,2:3,4-di-O-isopropylidene-β-D-arabinopyranose (2 g, 7.81 mmol) in dry tetrahydrofuran (15 ml) is added a 10 M solution of borane in methyl sulfide (0.78 ml, 7.8 mmol) at 0° C. under nitrogen. The mixture is stirred during 3 h at room temperature. The excess of borane is destroyed with ethanol (3 ml). The mixture is cooled at 0° C. 30% hydrogen peroxide (1 ml) and 3 N aqueous solution of sodium hydroxide (1 ml) are added. The mixture is refluxed during 2 h. The reaction mixture is diluted with water and extracted three times with ethyl acetate. The organic layer is dried over sodium sulfate, filtered and concentrated under reduced pressure so as to afford an oil. Flash chromatography on silica gel and elution with a 1:1 mixture of ethyl acetate and hexane will afford the expected alcohol 1,2:3,4-di-O-isopropylidene-1-(2-hydroxyethyl)-β-D-arabinopyranose as an oil.

EXAMPLE 47

Preparation of 1,2:3,4-DI-O-ISOPROPYLIDENE-1-(2-IODOETHYL)-α-D-ARABINOPYRANOSE

To a solution of 1,2,3,4-di-O-isopropylidene-1-(2-hydroxyethyl)-α-D-arabinose (1.7 g, 6.2 mmol) in dry methylene chloride (30 ml) is added triethylamine (1.3 ml, 9.3 mmol). Then the mixture is cooled to −10° C. and mesylchloride (0.5 ml, 6.46 mmol) is added dropwise. The mixture is stirred an additional 15 min at −10° C., then the reaction is allowed to warm up to room temperature. The mixture is washed three times with water. The organic phase is dried over sodium sulfate, filtered and concentrated under reduced pressure so as to afford a yellow oil which can be used without purification. The crude 1,2,3,4-di-O-isopropylidene-1-(2-methylsulfohyloxyethyl)-α-D-arabinose is dissolved in ether (15 ml). To this mixture a 0.35 M solution of magnesium iodide in ether (53 ml) is added at 0° C. The mixture is stirred 15 min at 0° C. The excess of magnesium iodide is hydrolyzed with water. The reaction mixture is washed with aqueous sodium thiosulfate and water. The organic layer is dried over sodium sulfate, filtered and concentrated under reduced pressure so as to afford an oil. Flash chromatography on silica gel and elution with a 9:1 mixture of hexane and ethyl acetate will afford the expected iodide 1,2:3,4-di-O-isopropylidene-1-(2-iodoethyl)-β-D-arabinopyranose as a slightly yellow oil.

EXAMPLE 48

Preparation of 2,3,6-TRI-O-BENZYL-1,5-DIDEOXY-1,5-{[2-(1,2,3,4-DI-O-ISOPROPYLIDENE-1-β-D-ARABINOPYRANOSYL) ETHYL)IMINO)-D-GLUCITOL A solution of 1,2:3,4-di-O-isopropylidene-1-(2-iodoethyl)-β-D-arabinose (1.9 g, 4.95 mmol) and 2,3,6-tri-O-benzyl-1,5-dideoxy-1,5-imino-D-glucitol (0.714 g, 1.65 mmol) in dry dimethylformamide (10 ml) is heated at 80° C. overnight along with dry potassium carbonate (0.91 g, 6.6 mmol). The dimethylformamide is evaporated under reduced pressure. The residue is taken with ethyl acetate and washed twice with water. The organic layer is dried over sodium sulfate, filtered and concentrated under reduced pressure so as to afford an oil. Chromatography on neutral aluminum oxide activity III and elution with a graded mixture of hexane and ethyl acetate will afford the expected amine 2,3,6-tri-O-benzyl-1,5-dideoxy-1,5{[2-(1,2,3,4-di-O-isopropylidene-1-β-D -arabinopyranosyl)]imino}-D-glucitol as a foam.

EXAMPLE 49

Preparation of 2,3,6-TRI-O-BENZYL-1,5-DIDEOXY-1,5-{[2-(1-O-METHYL-1-α-DARABINOFURANOSYL)ETHYL] IMINO}-D -GLUCITOL 2,3,6-tri-O-benzyl-1,5-dideoxy-1,5-{[2-(1,2:3,4-di-O-isopropylidene-1-β-D-arabinopyranosyl) ethyl]imino}-D-glucitol (0.739 g, 1.072 mmol) is dissolved in methanol (60 ml) containing 5% of dry hydrochloric acid and is refluxed during 24 h. The reaction mixture is cooled to room temperature and neutralized with Amberlyst A26 OH⁻ form. The mixture is filtered and the solvent is evaporated under reduced pressure so as to give a foam. Flash chromatography on silica gel and elution with a graded mixture of ethyl acetate and methanol will afford the expected amine 2,3,6-tri-O-benzyl-1,5-dideoxy-1,5-{[2-(1-O-methyl-1-α-D-arabinofuranosyl)ethyl] -imino}-D-glucitol as a foam.

EXAMPLE 50

Preparation of 1,5-DIDEOXY-1,5-([2-(1-O-METHYL-1-α-D-ARABINOFURANOSYL)ETHYL]-IMINO)-D-GLUCITOL The amine 2,3,6-tri-O-benzyl-1,5-dideoxy-1,5-{[2-(1-O-methyl-1-α-D-arabinofuranosyl)ethyl]  imino}-D-glucitol (0.4 g, 0.642 mmol) is dissolved in a 9:1 mixture of methanol and water (20 ml). Palladium hydroxide 20% on charcoal (0.2 g) is added and the mixture is hydrogenated during 4 days at atmospheric pressure. The catalyst is removed by filtration and the solvents are evaporated under reduced pressure. Flash chromatography on silica gel and elution with a graded mixture of chloroform, methanol and water will afford the expected amine 1,5-dideoxy-1,5-([2-(1-O-methyl-1-α-D-arabinofuranosyl)ethyl] -imino}-D-glucitol as an amorphous solid.

EXAMPLE 51

Preparation of

METHYL 6-O-(4-O-ACETYL-2,3,6-TRI-O-BENZYL-α-D-GALACTOPYRANOSYL)-2,3,4-TRI-O-BENZYL-α-D-GLUCOPYRANOSIDE

Ethereal silver perchlorate (0.08 M, 76.9 ml, 6.15 mmol) is added With stirring at −30° C. to a solution of methyl 2,3,4-tri-O-benzyl-α-D-glucopyranoside (2.078 g, 4.48 mmol), 4-O-acetyl-2,3,6-tri-O-benzyl-α-D-galactopyranosyl chloride (2,859 g, 5.6 mmol) and 2,4,6-trimethylpyridine (0.81 ml, 6.15 mmol) in ether (20 ml). The mixture is stirred 15 min at −30° C. and silver chloride precipitated. The mixture is filtered through a celite pad, the solids are washed with ether, the filtrate is concentrated under reduced pressure. The residue is dissolved in methylene chloride and the organic layer is washed successively with aqueous sodium thiosulfate and water. The organic layer is dried over sodium sulfate, filtered and concentrated under reduced pressure so as to afford a foam. Flash chromatography on silica gel and elution with a graded mixture of hexane and ethyl acetate will afford methyl 6-O-(4-O-acetyl-2,3,6-tri-O-benzyl-α-D-galactopyranosyl)-2,3,4-tri-O-benzyl-α -D-glucopyranoside as a foam.

EXAMPLE 52

Preparation of

METHYL 2,3,4-TRI-O-BENZYL-6-O-(2,3,6-TRI-O-BENZYL-α-D-GALACTOPYRANOSYL)-α-D-GLUCOPYRANOSIDE

Methyl 6-O-(4-O-acetyl-2,3,6-tri-O-benzyl-α-D-galactopyranosyl)-2,3,4-tri-O-benzyl-α-D-glucopyranoside (2.314 g, 2.46 mmol) is dissolved in hot toluene (20 ml) and methanol (80 ml) is added, followed by a few drops of 1 M methanolic sodium methoxide. The mixture is stirred at room temperature during 2 h. The reaction mixture is made neutral with Amberlite IR 120 ($H^+$) resin, filtered and concentrated under reduced pressure so as to afford methyl 2,3,4-tri-O-benzyl-6-O-(2,3,6-tri-O-benzyl-α-D-galactopyranosyl)-α-D -glucopyranoside as an amorphous solid.

EXAMPLE 53

Preparation of

METHYL 6-O-(2,3,6-TRI-O-BENZYL-4-O-TRIFLUOROMETHYLSULFONYL-α-D-GALACTOPYRANOSYL)-2,3,4-TRI-O-BENZYL-α -D-GLUCOPYRANOSIDE

To a solution of dry pyridine (0.45 ml) in dry methylene chloride (40 ml) cooled to −15° C. is added trifluoromethane sulfonic anhydride (0.83 ml). The mixture is stirred during 15 min at −10° C., then methyl 2,3,4-tri-O-benzyl-6-O-(2,3,6-tri-O-benzyl-α-D -galactopyranosyl)-α-D-glucopyranoside (2.21 g, 2.46 mmol) in methylene chloride (10 ml) is added. The mixture is washed with water. The organic layer is dried over sodium sulfate, filtered and concentrated under reduced pressure so as to afford an oil which will be the expected trillate methyl 6-O-(2,3,6-tri-O-benzyl-4-O-trifluoromethylsulfonyl-α-D-galactopyranosyl) -2,3,4-tri-O-benzyl-α-D-glucopyranoside.

EXAMPLE 54

Preparation of 2,3,6-TRI-O-BENZYL-1,5-DIDEOXY-N-[2,3,6-TRI-O-BENZYL-DEOXY-1-(2,3,4-TRI-O-BENZYL-1-O-METHYL-6 -O-α-D-GLUCOPYRANOSYL)-α-D-GLUCOPYRANOSYL]-1,5-IMINO-D-GLUCITOL A solution of methyl 6-O-(2,3,6-tri-O-benzyl-4-O-trifluoromethylsulfonyl-α-D-galactopyranosyl)-2,3,4-tri-O-benzyl -α-D-glucopyranoside (1.6g, 1.55 mmol) and 2,3,6-tri-O-benzyl-1,5-dideoxy-1,5-imino-D-glucitol (0.671 g, 1.55 mmol) in ethanol-free chloroform (50 ml) is refluxed under nitrogen during 48 h . The mixture is diluted in methylene chloride and washed successively with a saturated aqueous solution of sodium bicarbonate and saturated brine. The organic layer is dried over sodium sulfate, filtered and concentrated under reduced pressure so as to afford a foam. Flash chromatography on silica gel and elution with a graded mixture of hexane and ethyl acetate will afford the expected amine 2,3,6-tri-O-benzyl-1,5-dideoxy-N-[2,3,6-tri-O-benzyl-4-deoxy-1-(2,3,4 -tri-O-benzyl-1-O-methyl-6-O- α-D-glucopyranosyl)-α-D-glucopyranosyl] -1,5-imino-D-glucitol as an amorphous solid.

EXAMPLE 55

Preparation of 1,5-DIDEOXY-N-[4-DEOXY-1-(1-O-METHYL-6-O-α-D-GLUCOPYRANOSYL)-α-D-GLUCOPYRANOSYL]-1,5-IMINO-D -GLUCITOL 2,3,6-tri-O-benzyl-1,5-dideoxy-N-[2,3,6-tri-O-benzyl-4-deoxy-1-(2,3,4-tri-O-benzyl-1-O-methyl -6-O-α-D-glucopyranosyl)-α-D-glucopyranosyl]-1,5-imino-D-glucitol (1.2 g, 0.915 mmol) is dissolved in methanol (30 ml). Palladium hydroxide 20% on charcoal (0.6 g) is added. The mixture is hydrogenated during 4 days at 3 atmospheres. The catalyst is removed by filtration and the solvents are evaporated under reduced pressure. Flash chromatography on silica gel and elution with a graded mixture of chloroform, methanol and water will afford the expected amine 1,5-dideoxy-N-[4-deoxy-1-(1-O-methyl-6-O-α-D-glucopyranosyl) -α-D-glucopyranosyl]-1,5-imino-D-glucitol as an amorphous solid.

EXAMPLE 56

Preparation of 2,3,6-TRI-O-BENZYL-4-DEOXY-4-HYDROXYMETHYL-D-GLUCOPYRANOSE

Methyl 2,3,6-tri-O-benzyl-4-deoxy-4-hydroxymethyl-α-D-glucopyranoside (4.78 g, 10 mmol) is dissolved at 0° C. in a 9:1 mixture of trifluoroacetic acid and water (50 ml). The mixture is stirred overnight at 0° C. The solvents are evaporated under reduced pressure without heating. The residue is dissolved in ethyl acetate and washed successively with sodium bicarbonate and brine. The organic layer is dried over sodium sulfate, filtered and concentrated under reduced pressure so as to afford an oil. Flash chromatography on silica gel and elution with a graded mixture of ethyl acetate and hexane will afford 2,3,6-tri-O-benzyl-4-deoxy-4-hydroxy-methyl-D-glucopyranose as an oil.

EXAMPLE 57

Preparation of

ACETYL 2,3,6-TRI-O-BENZYL-4-DEOXY-4-ACETYLOXYMETHYL-D-GLUCO-PYRANOSIDE 2,3,6-tri-O-benzyl-4-deoxy-4-hydroxymethyl-D-glucopyranose (5.10 g, 9.30 mmol) is dissolved in dry pyridine (25 ml) and acetic anhydride (5 ml) is added. The mixture is stirred during 24 h at room temperature. The solvent is evaporated under high vacuum. The residue is dissolved in ethyl acetate and washed with water. The organic layer is dried over sodium sulfate, filtered and concentrated under reduced pressure so as to afford the expected diacetate acetyl 2,3,6-tri-O-benzyl-4-deoxy-4-acetyloxymethyl-D-glucopyranoside as an oil which is used without purification.

EXAMPLE 58

Preparation of 2,3,6-TRI-O-BENZYL-1,4-DIDEOXY-4-ACETYLOXYMETHYL-D-GLUCOPYRANOSYL CHLORIDE Acetyl 2,3,6-tri-O-benzyl-4-deoxy-4-acetyloxymethyl-D-glucopyranoside (5.10 g, 9.30 mmol) in ether (10 ml) is treated with ethereal hydrogen chloride (0.2 g/ml, 25 ml). The mixture is stirred at room temperature during 48 h. The solvents are evaporated under reduced pressure so as to afford an oil. Flash chromatography on silica gel and elution with a graded mixture of carbon tetrachloride and ethyl acetate will afford 2,3,6-tri-O-benzyl-1,4-dideoxy-4-acetyloxymethyl-D-glucopyranosyl chloride as an oil.

EXAMPLE 59

Preparation of

METHYL 4-O-(2,3,6-TRI-O-BENZYL-4-DEOXY-4-ACETYLOXYMETHYL-α-D-GLUCOPYRANOSYL)-2,3,6-TRI-O-BENZYL-α -D-GLUCOPYRANOSIDE

Ethereal silver perchlorate (0.08 M, 9.58 ml, 7.67 mmol) is added with stirring at −30° C. to a solution of methyl 2,3,6-tri-O-benzyl-α-D-glucopyranoside (2.592 g, 5.59 mmol), 2,3,6-tri-O-benzyl-1,4-dideoxy-4-acetyloxymethyl-D-gluco-pyranosyl chloride (3.661 g, 6.98 mmol) in ether (20 ml). The mixture is stirred 15 min at −30° C. and silver chloride precipitated. The mixture is filtered through a celite pad, the solids are washed with ether, the filtrate is concentrated under reduced pressure. The residue is dissolved in methylene chloride and the organic layer is washed successively with aqueous sodium thiosulfate and water. The organic layer is dried over sodium sulfate, filtered and concentrated under reduced pressure so as to afford a foam. Flash chromatography on silica gel and elution with a graded mixture of hexane and ethyl acetate will afford methyl 4-O-(2,3,6-tri-O-benzyl-4-deoxy-4-acetyloxymethyl-α-D-glucopyranosyl)-2,3,6 -tri-O-benzyl-α-D-glucopyranoside as a foam.

EXAMPLE 60

Preparation of

METHYL 4-O-(2,3,6-TRI-O-BENZYL-4-DEOXY-4-HYDROXYMETHYL-α-D-GLUCOPYRANOSYL)-2,3,6-TRI-D-BENZYL-α -D-GLUCOPYRANOSIDE

Methyl 4-O-(2,3,6-tri-O-benzyl-4-deoxy-4-acetyloxymethyl-α-D-glucopyranosyl)-2,3,6-tri-O-benzyl-α -D-glucopyranoside (3.19 g, 3.35 mmol) is dissolved in hot toluene (20 ml) and methanol (80 ml) is added, followed by a few drops of 1 M methanolic sodium methoxide. The mixture is stirred at room temperature during 2 h. The reaction mixture is made neutral with Amberlite IR 120 (H⁺) resin, filtered and concentrated under reduced pressure so as to afford methyl 4-O-(2,3,6-tri-O-benzyl-4-deoxy-4-hydroxymethyl-α-D-glucopyranosyl)-2,3,6-tri-O-benzyl-α -D-glucopyranoside as an amorphous solid.

EXAMPLE 61

Preparation of

METHYL 4-O-(2,3,6-TRI-O-BENZYL-4-DEOXY-4-TRIFLUOROMETHYL-SULFONYLOXYMETHYL-α-D-GLUCOPYRANOSYL)-2,3,6-TRI -O-BENZYL-α-D-GLUCOPYRANOSIDE

To a solution of dry pyridine (0.6 ml) in dry methylene chloride (50 ml) cooled to −15° C. is added trifluoromethane sulfonic anhydride (1.12 ml). The mixture is stirred during 15 min at −10° C., then methyl 4-O-(2,3,6-tri-O-benzyl-4-deoxy-4-hydroxymethyl-α-D -glucopyranosyl)-2,3,6-tri-O-benzyl-α-D-glucopyranoside (3.049g, 3.35 mmol) in methylene chloride (15 ml)is added. The mixture is washed with water. The organic layer is dried over sodium sulfate, filtered and concentrated under reduced pressure so as to afford an oil which will be the expected triflate methyl 4-O-(2,3,6-tri-O-benzyl-4-deoxy-4-trifluoromethyl-sulfonyloxymethyl-α-D-glucopyranosyl)-2,3,6 -tri-O-benzyl-α-D-glucopyranoside.

EXAMPLE 62

Preparation of 2,3,6-TRI-O-BENZYL-1,5-DIDEOXY-N-{[2,3,6-TRI-O-BENZYL-4-DEOXY-1-(2,3,6-TRI-O-METHYL-4-O -α-D-GLUCOPYRANOSYL)-4-α-D-GLUCOPYRANOSYL]METHYL)-1,5-IMINO-D-GLUCITOL A solution of methyl 4-O-(2,3,6-tri-O-benzyl-4-deoxy-4-trifluoromethylsulfonyloxymethyl-α-D-glucopyranosyl) -2,3,6-tri-O-benzyl-α-D-glucopyranoside (1.82 g, 1.75 mmol) and 2,3,6-tri-O-benzyl-1,5-dideoxy-1,5-imino-D-glucitol (0.758 g, 1.75 mmol) in ethanol-free chloroform (50 ml) is refluxed under nitrogen during 48 h. The mixture is diluted in methylene chloride and washed successively with a saturated brine. The organic layer is dried over sodium sulfate, filtered and concentrated under reduced pressure so as to afford a foam. Flash chromatography on silica gel and elution with a graded mixture of hexane and ethyl acetate will afford the expected amine 2,3,6-tri-O-benzyl-1,5-dideoxy-N-{[2,3,6-tri-O-benzyl-4-deoxy-1 -(2,3,6-tri-O-benzyl-4-O-α-D-glucopyranosyl)-4-α-D-glucopyranosyl]methyl}1,5-imino-D-glucitol as an amorphous solid.

EXAMPLE 63

Preparation of 1.5-DIDEOXY-N-{[4-DEOXY-1-(1-O-METHYL-4-O-α-D-GLUCOPYRANOSYL)-4-α-D-GLUCOPYRANOSYL]METHYL}1,5-IMINO-D-GLUCITOL 2,3,6-tri-O-benzyl-1,5-dideoxy-N-([2,3,6-tri-O-benzyl-4-deoxy-1-(2,3,6-tri-O-benzyl-1-O -methyl-4-O-α-D-glucopyranosyl)-4-α-D-glucopyranosyl]methyl}1,5-imino-D-glucitol (1.3 g, 1.247 mmol) is dissolved in methanol (40 ml). Palladium hydroxide 20% on charcoal (0.6 g) is added. The mixture is hydrogenated during 4 days at 3 atmospheres. The catalyst is removed by filtration and the solvents are evaporated under reduced pressure. Flash chromatography on silica gel and elution with a graded mixture of chloroform, methanol and water will afford the expected amine 1,5-dideoxy-N-([4-deoxy-1-(1-O-methyl-4-O-α-D -glucopyranosyl)-4-α-D-glucopyranosyl]methyl}1,5-imino-D-glucitol as an amorphous solid.

EXAMPLE 64

Preparation of

METHYL 6-O-(2,3,6-TRI-O-BENZYL-4-DEOXY-4-ACETYLOXYMETHYL-α-D-GLUCOPYRANOSYL)-2,3,4-TRI-O-BENZYL-α -D-GLUCOPYRANOSIDE

Ethereal silver perchlorate (0.08 M, 76.7 ml, 6.13 mmol) is added with stirring at −30° C. to a solution of methyl 2,3,4-tri-O-benzyl-α-D-glucopyranoside (2.074 g, 4.472 mmol), 2,3,6-tri-O-benzyl-1,4-dideoxy-4-acetyloxymethyl-D-gluco-pyranosyl chloride (6.13 mmol) and 2,4,6trimethylpyridine (0.80 ml, 6.13 mmol) in ether (20 ml). The mixture is stirred 15 min at −30° C. and silver. chloride precipitated. The mixture is filtered through a celite pad, the solids are washed with ether, the filtrate is concentrated under reduced pressure. The residue is dissolved in methylene chloride and the organic layer is washed successively with aqueous sodium thiosulfate and water. The organic layer is dried over sodium sulfate, filtered and concentrated under reduced pressure so as to afford a foam. Flash chromatography on silica gel and elution with a graded mixture of hexane and ethyl acetate will afford methyl 6-O-(2,3,6-tri-O-benzyl-4-deoxy-4-acetyloxymethyl-α-D-glucopyranosyl)-2,3,4-tri-O -benzyl-α-D-glucopyranoside as a foam.

EXAMPLE 65

Preparation of

METHYL 6-O-(2,3,6-TRI-O-BENZYL-4-DEOXY-4-HYDROXYMETHYL-α-GLUCOPYRANOSYL)-2,3,4-TRI-O-BENZYL-α-D -GLUCOPYRANOSIDE

Methyl 6-O-(2,3,6-tri-O-benzyl-4-deoxy-4-acetytoxymethyl-α-D-glucopyranosyl)-2,3,4-tri-O-benzyl -α-D-glucopyranoside (2.469 g, 2.593 mmol) is dissolved in hot toluene (20 ml) and methanol (80 ml) is added, followed by a few drops of 1 M methanolic sodium methoxide. The mixture is stirred at room temperature during 2 h. The reaction mixture is made neutral with Amberlite IR 120 (H+) resin, filtered and concentrated under reduced pressure so as to afford methyl 6-O-(2,3,6-tri-O-benzyl-4-deoxy-4-hydroxymethyl-α-D-glucopyranosyl)-2,3,4-tri-O -benzyl-α-D-glucopyranoside as an amorphous solid.

EXAMPLE 66

Preparation of

METHYL 6-O-(2,3,6-TRI-O-BENZYL-4-DEOXY-4-TRIFLUOROMETHYL-SULFONYLOXYMETHYL-α-D-GLUCOPYRANOSYL)-2,3,4-TRI-O -BENZYL-α-D-GLUCOPYRANOSIDE

To a solution of dry pyridine (0.46 ml) in dry methylene chloride (40 ml) cooled to −15° C. is added trifluoromethane sulfonic anhydride (0.86 ml). The mixture is stirred during 15 min at −10° C., then methyl 6-O-(2,3,6-tri-O-benzyl-4-deoxy-4-hydroxymethyl-α-D -glucopyranosyl)2,3,4-tri-O-benzyl-α-D-glucopyranoside (2.36 g, 2.593 mmol) in methylene chloride (10 ml) is added. The mixture is stirred during 1.5 h at −10° C. The reaction mixture is washed with water. The organic layer is dried over sodium sulfate, filtered and concentrated under reduced pressure so as to afford an oil which will be the expected triflate methyl 6-O-(2,3,6-tri-O-benzyl-4-deoxy-4-trifluoromethylsulfonyloxymethyl -α-D-glucopyranosyl)-2,3,4-tri-O -benzyl-α-D-glucopyranoside.

EXAMPLE 67

Preparation of 2,3,6-TRI-O-BENZYL-1,5-DIDEOXY-N-([2,3,6,TRI-O-BENZYL-4-DEOXY-1-(2,3,4-TRI-O-BENZYL-1-O-METHYL -6-O-α-D-GLUCOPYRANOSYL)-4-α-D-GLUCOPYRANOSYL]METHYL)1,5-IMINO-D-GLUCITOL A solution of methyl 6-O-(2,3,6-tri-O-benzyl-4-deoxy-4-trifluoromethylsulfonyloxymethyl-α-D-glucopyranosyl) -2,3,4-tri-O-benzyl-α-D-glucopyranoside (1.8 g, 1.72 mmol) and 2,3,6-tri-O-benzyl-1, 5-dideoxy-1,5-imino-D-glucitol (0.745 g, 1.72 mmol) in ethanol-free chloroform (50 ml) is refluxed under nitrogen during 48 h. The mixture is diluted in methylene chloride and washed successively with a saturated aqueous solution of sodium bicarbonate and saturated brine. The organic layer is dried over sodium sulfate, filtered and concentrated under reduced pressure so as to afford a foam. Flash chromatography on silica gel and elution with a graded mixture of hexane and ethyl acetate will afford the expected amine 2,3,6-tri-O-benzyl-1,5-dideoxy-N-([2,3,6-tri-O-benzyl-4-deoxy-1 -(2,3,4-tri-O-benzyl-1-O-methyl-6-O-α-D-glucopyranosyl)-4-α-D-glucopyranosyl]methyl}1,5-imino-D -glucitol as an amorphous solid.

EXAMPLE 68

Preparation of 1,5-DIDEOXY-N-{[4-DEOXY-1-(1-O-METHYL-6-O-α-D-GLUCOPYRANOSYL)-4-α-D-GLUCOPYRANOSYL]METHYL }1,5-IMINO-D-GLUCITOL 2,3,6-tri-O-benzyl-1,5-dideoxy-N-([2,3,6-tri-O-benzyl-4-deoxy-1-(2,3,4-tri-O-benzyl-1-O-methyl -6-O-α-D-glucopyranosol)-4-α-D-glucopyranosyl]methyl}1,5-imino-D-glucitol (1.3 g, 1.247 mmol) is dissolved in methanol (30 ml). Palladium hydroxide 20% on charcoal (0.6 g) is added. The mixture is hydrogenated during 4 days at 3 atmospheres. The catalyst is removed by filtration and the solvents are evaporated under reduced pressure. Flash chromatography on silica gel and elution with a graded mixture of chloroform, methanol and water will afford the expected amine 1,5-dideoxy-N-{[4-deoxy-1-(1-O-methyl-6-O-α-D -glu-copyranosyl)-4-α-D-glucopyranosyl]methyl}1,5-imino-D-glucitol as an amorphous solid.

EXAMPLE 69

Preparation of

1,5-DIDEOXY-1,5-(6-DEOXY-6-D-GLUCOPYRANO-SYL)IMINO-D-GLUCITOL 1,5-dideoxy-1,5-(6-deoxy-1-O-methyl-6-α-D-glucopyranosyl)imino-D-glucitol (0.150 g, 0.442 mmol) is dissolved in a 1:1 mixture of water and trifluoroacetic acid (10 ml). The mixture is stirred during 24 h at 0° C. The solvents are evaporated under reduced pressure so as to afford a foam. Chromatography on Amberlyst A26 OH⁻ form will afford the expected amine 1,5-dideoxy-1,5-(6-deoxy-6-D-glucopyranosyl)imino-D-glucitol.

EXAMPLE 70

Preparation of

5-AZIDO-3,6-DI-O-BENZYL-5-DEOXY-D-GLUCOFURANOSE

The azide 5-azido-3,6-di-O-benzyl-5-deoxy-1,2-O-isopropylidene-α-D-glucofuranoside (U. G. Nayak and R. L. Whisler, *J. Org. Chem.*, 33, 3582 (1968) (15.02 g, 35.3 mmol) was dissolved at 0° C. in 100 ml of a 9:1 mixture of trifluoroacetic acid and water. The mixture was stirred at 0° C. during 2 h. The trifluoroacetic acid was evaporated under reduced pressure at room temperature. The residue was taken with ether and washed with water. The organic layer was dried over sodium sulfate, filtered and concentrated under reduced pressure. Flash chromatography on silica gel and elution with a 1:1 mixture of hexane and ethyl acetate, followed by recrystallization in a mixture of hexane and ethyl acetate afforded the expected compound 5-azido-3,6-di-O-benzyl-5-deoxy-D-glucofuranose.

EXAMPLE 71

Preparation of

METHYL 5-AZIDO-3,6-DI-O-BENZYL-5-DEOXY-D-GLUCOFURANOSIDE

To a solution of 5-azido-3,6-di-O-benzyl-5-D-glucofuranose (10.23 g, 26.5 mmol) in methylene chloride (170 ml) was added methanol (11 ml) and borontrifluoroetherate (1.5 ml). The mixture was stirred 24 h at room temperature. The reaction mixture was successively washed with a saturated aqueous solution of sodium bicarbonate and then with brine. The organic layer was dried over sodium sulfate, filtered and concentrated under reduced pressure. Flash chromatography on silica gel and elution with a 1:1 mixture of hexane and ethyl acetate afforded methyl 5-azido-3,6-di-O-benzyl-5-deoxy-D-glucofuranoside as colorless oil (9.15 g, 85%).

EXAMPLE 72

Preparation of

METHYL 5-AZIDO-2,3,6-TRI-O-BENZYL-5-DEOXY-D-GLUCOFURANOSIDE

To a suspension of sodium hydride (1.2 g, 27.5 mmol), 55% in mineral oil, washed three times with pentane) in anhydrous tetrahydrofuran (200 ml) was added quickly dropwise the alcohol methyl 5-azido-3,6-di-O-benzyl-5-deoxy-D-gluco-furanoside (9.15 g, 22.9 mmol) in tetrahydrofuran (50 ml) at room temperature and under nitrogen. The mixture was stirred during 3 h at room temperature. the mixture was yellow. Then n-Bu₄N⁺I⁻ (76 mg, 0.20 mmol) was added followed by benzyl bromide (3.30 ml, 27.5 mmol) added dropwise. The mixture was stirred overnight at room temperature. After hydrolysis with saturated aqueous ammonium chloride tetrahydrofuran was evaporated under reduced pressure. The residue was diluted with water and extracted three times with ether. The organic phase was dried over sodium sulfate. Filtration and evaporation under reduced pressure afforded an oil. Flash chromatography on silica gel and elution with a 20:80 mixture of ethyl acetate and hexane afforded the expected compound methyl 5-azido-2,3, 6-tri-O-benzyl-5-deoxy-D-glucofuranoside as a colorless oil (10.88 g, 97%).

EXAMPLE 73

Preparation of

5-AZIDO-2,3,6-TRI-O-BENZYL-5-DEOXY-D-GLUCOFURANOSE

Methyl 5-azido-2,3,6-tri-O-benzyl-5-deoxy-D-glucofurano-side (10.8 g, 22.2 mmol) was dissolved at room temperature in tetrahydrofuran (20 ml). The solution was cooled at −10° C. and trifluoroacetic acid (120 ml) was added dropwise followed by addition of water (20 ml). The mixture was stirred at 0° C. during 24 h. The mixture was evaporated under reduced pressure without heating. The residue was taken with ether and washed with water. The organic layer was dried over sodium sulfate, filtered and concentrated under reduced pressure. Flash chromatography on silica gel and elution with a 20:80 mixture of ethyl acetate and hexane afforded 5-azido-2,3,6-tri-O-benzyl-5-deoxy-D-glucofuranose as a colorless oil (9.63 g, 90%).

EXAMPLE 74

Preparation of

5-AZIDO-2,3,6-TRI-O-BENZYL-5-DEOXY-D-GLUCONIC ACID-γ-LACTONE

To a solution of the lactol 5-azido-2,3,6-tri-O-benzyl-5-deoxy-D-glucofuranose (9.36 g, 20 mmol) in acetone (240 ml) cooled to 0° C., Jones' reagent 2 M (11.5 ml) was added dropwise until the color was orange. The excess of Jones' reagent was destroyed with 2-propanol (0.5 ml). The mixture was concentrated under reduced pressure. The residue was taken with water and extracted with ether. The organic phase was dried with sodium sulfate, filtered and concentrated under reduced pressure so as to afford an oil. Flash chromatography on silica gel and elution with a 1:9 mixture of ethyl acetate and hexane afforded the γ-lactone 5-azido-2,3,6-tri-O-benzyl-5-deoxy-D-gluconic acid-γ-lactone.

EXAMPLE 75

Preparation of

2,3,6-TRI-O-BENZYL-5-DEOXY-D-GLUCONIC ACID-δ-LACTAM

To a solution of the lactone 5-azido-2,3,6-tri-O-benzyl-5-deoxy-D-gluconic acid-γ-lactone (8.16 g, 17 mmol) in ethanol (180 ml) was added lindlar catalyst (1.7 g). The mixture was hydrogenated under atmospheric pressure during 24 h. Filtration and evaporation under reduced pressure afforded an oil which was crystallized in a mixture of hexane and ether. The lactam 2,3,6-tri-O-benzyl-5-deoxy-D-gluconic acid-δ-lactam was obtained as white crystals (7.4 g, 96%). mp: 85°–85.5° C.

By substituting those specifically mentioned final products set forth above which are analogous to 1,5-dideoxy-1,5-[(6-deoxy-1-O-methyl-6-α-D -glucopyranosyl)imino]-D-glucitol and by following the teachings of Examples 2 through 6, there will be produced the final compounds of this invention (Formula I) which are analogous to the final compound of Example 6. Similarly, by preparing the appropriately positioned bromo derivative (analogous to methyl-6-bromo-6-deoxy-α-D-glucopyranoside of Example 1) of the above mentioned glycosyl moieties utilized for the condensations reactions with 1-deoxy nojirimycin, and by following the teachings of Example 1, there will be produced the final products analogous to the product of Example 1. these compounds are set forth as follows:

1,5-Dideoxy-4-O(α,D-glucopyranosyl)-1,5-[6,7-dideoxy-7-D-glucoheptopyranosyl)imino]-D-glucitol, 1,5-Dideoxy-4-O(α,D-glucopyranosyl)-1,5-[(1-deoxy-D-fructofuranosyl)imino]-D-glucitol, 1,5-Dideoxy-4-O(α,D-glucopyranosyl)-1,5-[(4-deoxy-4-D-glucopyranosyl)imino]-D-glucitol, 1,5-Dideoxy-4-O(α,D-glucopyranosyl)-N-[6-deoxy-1-(6-O-D-glucopyranosyl)-α-D-glucopyranosyl] -1, 5-imino-D-glucitol, 1,5-Dideoxy-4-O(α,D-glucopyranosyl)-N-[6,7-dideoxy-1-(6-O-D-glucopyranosyl)-7-α-D -glucoheptopyranosyl]-1, 5-imino-D-glucitol, 1,5-Dideoxy-4-O(α,D-glucopyranosyl)-1,5-[(4-deoxy-4-D-glucopyranosyl)methylimino]-D-glucitol, 1,5-Dideoxy-4-O(α,D-glucopyranosyl)-N-[4-deoxy-1-(4-O-D-glucopyranosyl)-α-D-glucopyranosyl] -1,5-imino-D-glucitol, 1,5-Dideoxy-4-O(α,D-glucopyranosyl)-1,5-{[2(1-D-arabinofuranose)ethyl]imino}-D-glucitol, 1,5-Dideoxy-4-O(α,D-glucopyranosyl)-N-[4-deoxy-1-(6-O-D-glucopyranosyl)-α-D-glucopyranosyl] -1,5-imino-D-glucitol, 1,5-Dideoxy-4-O(α,D-glucopyranosyl)-N-{[4-deoxy-1-(4-O-D-glucopyranosyl)-4-α-D -glucopyranosyl]methyl}-1, 5-imino-D-glucitol, 1,5-Dideoxy-4-O(α,D-glucopyranosyl)-N-{[4-deoxy-1-(6-O-D-glucopyranosyl)-4-α-D -glucopyranosyl]methyl}-1, 5-imino-D-glucitol, 1,5-Dideoxy-4-O(α,D-glucopyranosyl)-1,5-[(6-deoxy-1-O-methyl-6-β-D-glucopyranosyl)-imino-D -glucitol, 1,5-Dideoxy-4-O(α,D-glucopyranosyl)-1,5-[(6,7-dideoxy-1-O-methyl-7-β-D-glucoheptopyranosyl) imino]-D-glucitol, 1,5-Dideoxy-4-O(α,D-glucopyranosyl)-1,5-[(1-deoxy-2-O-methyl-β-D-fructofuranosyl)imino] -D-glucitol, 1,5-Dideoxy-4-O(α,D-glucopyranosyl)-1,5-[(4-deoxy-1-O-methyl-4-β-D-glucopyranosyl)imino] -D-glucitol, 1,5-Dideoxy-4-O(α,D-glucopyranosyl)-N-[6-deoxy-1-(1-O-methyl-6-O-β-D-glucopyranosyl)-α-D -glucopyranosyl]-1,5-imino-D-glucitol, 1,5-Dideoxy-4-O(α,D-glucopyranosyl)-N-[6,7-dideoxy-1-(1-O-methyl-6-O-β-D-glucopyranosyl)-7 -α-D-glucoheptopyranosyl]-1,5-imino-D-glucitol, 1,5-Dideoxy-4-O(α,D-glucopyranosyl)-1,5-[(4-deoxy-1-O-methyl-4-β-D-glucopyranosyl)methylimino] -D-glucitol, 1,5-Dideoxy-4-O(α,D-glucopyranosyl)-N-[4-deoxy-1-(1-O-methyl-4-O-8-D-glucopyranosyl)-α-D -glucopyranosyl]-1,5-imino-D-glucitol, 1,5-Dideoxy-4-O(α,D-glucopyranosyl)-1,5-{[2-(1-O-methyl-1-β-D-arabinofuranosyl)ethyl] imino}-D-glucitol, 1,5-Dideoxy-4-O(α,D-glucopyranosyl)-N-[4-deoxy-1-(1-O-methyl-6-O-β-D-glucopyranosyl)-α -D-glucopyranosyl]-1,5-imino-D-glucitol, 1,5-Dideoxy-4-O(α,D-glucopyranosyl)-N-{[4-deoxy-1-(1-O-methyl-4-O-β-D-glucopyranosyl)-4 -α-D-glucopyranosyl]methyl}-1,5-imino-D-glucitol, 1,5-Dideoxy-4-O(α,D-glucopyranosyl)-N-{[4-deoxy-1-(1-O-methyl-6-O-β-D-glucopyranosyl)-4 -α-D-glucopyranosyl]methyl}-1,5-imino-D-glucitol, 1,5-Dideoxy-6-O(α,D-glucopyranosyl)-1,5-[6,7-dideoxy-7-D-glucoheptopyranosyl)imino]-D-glucitol, 1,5-Dideoxy-6-O(α,D-glucopyranosyl)-1,5-[(1-deoxy-D-fructofuranosyl)imino]-D-glucitol, 1,5-Dideoxy-6-O(α,D-glucopyranosyl)-1,5-[(4-deoxy-4-D-glucopyranosyl)imino]-D-glucitol, 1,5-Dideoxy-6-O(α,D-glucopyranosyl)-N-[6-deoxy-1-(6-O-D-glucopyranosyl)-α-D-glucopyranosyl] -1,5-imino-D-glucitol, 1,5-Dideoxy-6-O(α,D-glucopyranosyl)-N-[6,7-dideoxy-1-(6-O-D-glucopyranosyl)-7-α-D -glucoheptopyranosyl]-1, 5-imino-D-glucitol, 1,5-Dideoxy-6-O(α,D-glucopyranosyl)-1,5-[(4-deoxy-4-D-glucopyranosyl)methylimino]-D-glucitol, 1,5-Dideoxy-6-O(α,D-glucopyranosyl)-N-[4-deoxy-1-(4-O-D-glucopyranosyl)-α-D-glucopyranosyl] -1,5-imino-D-glucitol, 1,5-Dideoxy-6-O(α,D-glucopyranosyl)-1,5-{[2(1-D-arabinofuranose)ethyl]imino}-D-glucitol, 1,5-Dideoxy-6-O(α,D-glucopyranosyl)-N-[4-deoxy-1-(6-O-D-glucopyranosyl)-α-D-glucopyranosyl] -1,5-imino-D-glucitol, 1,5-Dideoxy-6-O(α,D-glucopyranosyl)-N-{[4-deoxy-1-(4-O-D-glucopyranosyl)-4-α-D -glucopyranosyl]methyl}-1, 5-imino-D-glucitol, 1,5-Dideoxy-6-O(α,D-glucopyranosyl)-N-{[4-deoxy-1-(6-O-D-glucopyranosyl)-4-α-D -glucopyranosyl]methyl}-1, 5-imino-D-glucitol, 1,5-Dideoxy-6-O(α,D-glucopyranosyl)-1,5-[(6-deoxy-1-O-methyl-6-β-D-glucopyranosyl) -imino-D-glucitol, 1,5-Dideoxy-6-O(α,D-glucopyranosyl)-1,5-[(6,7-dideoxy-1-O-methyl-7-β-D-glucoheptopyranosyl) imino]-D-glucitol, 1,5-Dideoxy-6-O(α,D-glucopyranosyl)-1,5-[(1-deoxy-2-O-methyl-β-D-fructofuranosyl)imino]-D-glucitol, 1,5-Dideoxy-6-O(α,D-glucopyranosyl)-1,5-[(4-deoxy-1-O-methyl-4-β-D-glucopyranosyl)imino] -D-glucitol, 1,5-Dideoxy-6-O(α,D-glucopyranosyl)-N-[6-deoxy-1-(1-O-methyl-6-O-β-D-glucopyranosyl)-α-D -glucopyranosyl]-1,5-imino-D-glucitol, 1,5-Dideoxy-6-O(α,D-glucopyranosyl)-N-[6,7-dideoxy-1-(1-O-methyl-6-O-β-D-glucopyranosyl) -7-α-D-glucoheptopyranosyl]-1,5-imino-D-glucitol, 1,5-Dideoxy-6-O(α,D-glucopyranosyl)-1,5-[(4-deoxy-1-O-methyl-4-β-D-glucopyranosyl)methylimino]-D-glucitol, 1,5-Dideoxy-6-O(α,D-glucopyranosyl)-N-[4-deoxy-1-(1-O-methyl-4-O-β-D-glucopyranosyl)-α-D -glucopyranosyl]-1,5-imino-D-glucitol, 1,5-Dideoxy-6-O(α,D-glucopyranosyl)-1,5-{[2-(1-O-methyl-1-B-D-arabinofuranosyl)ethyl]imino} -D-glucitol, 1,5-Dideoxy-6-O(α,D-glucopyranosyl)-N-[4-deoxy-1-(1-O-methyl-6-O-β-D-glucopyranosyl)-α-D -glucopyranosyl]-1,5-imino-D-glucitol, 1,5-Dideoxy-6-O(α,D-glucopyranosyl)-N-([4-deoxy-1-(1-O-methyl-4-O-β-D-glucopyranosyl)-4 -α-D-glucopyranosyl]methyl}-1,5-imino-D-glucitol, 1,5-Dideoxy-6-O(α,D-glucopyranosyl)-N-([4-deoxy-1-(1-O-methyl-6-O-β-D-glucopyranosyl)-4 -α-D-glucopyranosyl]methyl}-1,5-imino-D-glucitol.

Enzymes which catalyze the hydrolysis of complex carbohydrates, e.g. α-glycosidases, convert nonabsorbable carbohydrates into absorbable sugars. The rapid action of these enzymes, particularly following the intake of high levels of carbohydrates, lead to acute high levels in blood glucose which, in the case diabetics, lead to undesirable manifestations, thus it has been a long-sought goal to find compounds which will obviate the hyperglycemia caused by dietary improprieties. Similarly, in the case of obesity the control of high levels of blood glucose, with its subsequent conversion to fat, caused by the catalysis of carbohydrates has inspired the quest for compounds which will obviate the problems associated with dietary improprieties.

The compounds of this invention (I) are potent and long-lasting inhibitors of α-glucosidase and, by standard laboratory methods for determining serum glucose levels, are shown to be useful for the treatment of disease states caused by the under utilization and/or overproduction of serum glucose without adversely affecting the rate of transport across cell membranes. Thus, the compounds are useful in the treatment of diabetes and obesity.

In the practice of this invention, an effective amount of a compound of this invention is that amount required to reduce the amount of serum glucose (relative to a control) following the ingestion of carbohydrates convertible to absorbable glucose. The specific dosage for the treatment of any specific patient suffering from either disease state will depend upon such factors as size, type and age of the patient as well as the severity of the disease state, all of which are factors normally familiar to and considered by the attending diagnostician treating the patient. Generally, the compounds are to be administered orally at a dose of 0.2 to 20 milligrams per kilogram of body weight (MPK) with a dose of 0.5 to 5 MPK being preferred. The compounds preferable are to be administered orally at mealtimes in single or multiple unit doses containing 25 mg to 250 mg. Of course, in the treatment of obesity, the term includes the practice of the disease as well as continued administration of dose regimens suitable for the maintenance of the desired weight for the patient.

It is also to be found that the compounds of the instant invention (I) will exert an inhibitory effect on glycosidase enzymes that are essential for elaboration of the final structure of the oligosaccharide side-chains of glycoproteins, particularly the HIV (gp 120) glycoprotein. Suitable assay techniques, e.g. syncytial formation, the reverse transcriptase assay, immunofluorescence tests and election microscopy, may be used to evaluate the effects on HIV vital growth and for determining dose regimens. Antivital effects may be confirmed by immunofluorescence with serum for virally infected patients. In the treatment of the HIV related disease states, as well as other retroviral glycoprotein-related disease states, unlike the treatment of diabetes and obesity, the compounds of this invention may be administered by parenteral means; specific doses being within the above stated dose range for treatment of diabetes and obesity.

In practicing the end-use application of the compounds of this invention, the compounds are preferably incorporated in a pharmaceutical formulation comprising a pharmaceutical carrier in admixture with a compound of this invention. The term "pharmaceutical carrier" refers to known pharmaceutical excipients useful in formulating pharmaceutically active compounds for internal administration to animals, and which are substantially nontoxic and nonsensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired. Suitable pharmaceutical carriers and formulation techniques are found in standard texts, such as Remington's Pharmaceutical Sciences, Mack Publishing Company, Easton, Pa.

We claim:

1. A compound of the formula

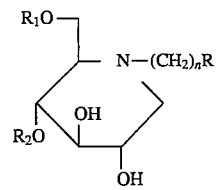

and the pharmaceutically acceptable acid addition salts thereof wherein n is zero, 1 or 2, R is a glycosyl moiety containing 1 to 3 hexose or penrose units, said units bearing a methoxy moiety at the anomeric carbon atom of the terminal hexose or pentose unit, and one of $R_1$ or $R_2$ is H and the other is α-D-glucopyranosyl.

2. A compound of claim 1 wherein $R_1$ is α-D-glucopyranosyl and $R_2$ is H.

3. A compound of claim 1 wherein $R_2$ is α-D-glucopyranosyl and $R_1$ is H.

4. A compound of claim 1 wherein n is one.

5. A compound of claim 1, said compound being 1,5-dideoxy-4-O-(α, D-glucopyranosyl)-1,5-[(6-deoxy-1-O-methyl-6-α,D-glucopyranosyl)imino]-D-glucitol.

6. A pharmaceutical composition comprising the compound according to any one of claims 1 through 5 and an acceptable pharmaceutical carrier.

7. A process for treating hyperglycemia which comprises administering to a patient suffering from hyperglycemia a therapeutically effective amount of a compound of claim 1.

8. A process for treating obesity which comprises administering to a patient suffering from obesity a therapeutically effective amount of a compound of claim 1.

9. A process for preparing a compound of the formula

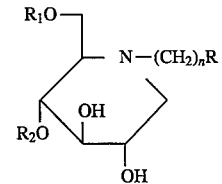

or the pharmaceutically acceptable acid addition salts thereof wherein n is zero, 1 or 2, R is a glycosyl moiety containing 1 to 3 hexose or pentose units, said units optionally bearing a methoxy moiety at the anomeric carbon atom of the terminal hexose or pentose unit, and one of $R_1$ and $R_2$ is H and the other is α-D-glucopyranosyl, which comprises the reactions (a) condensing a compound of the formula

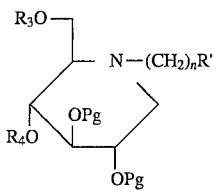  III wherein n is zero, one or two, R' is a glycosyl moiety as defined for R in Formula II wherein its OH radicals bear a hydroxy-protecting group, Pg is a hydroxy-protecting group, and one of $R_3$ and $R_4$ is a hydroxy-protecting group and the other is H, with a compound of the formula

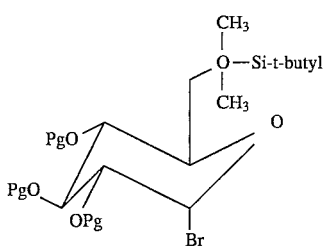  IV to produce a compound of the formulae

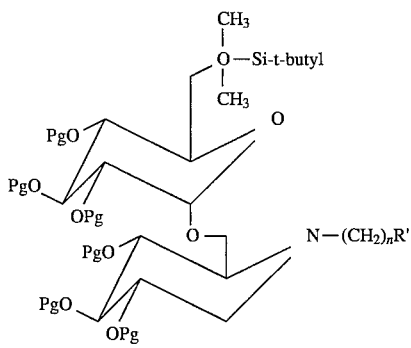  V

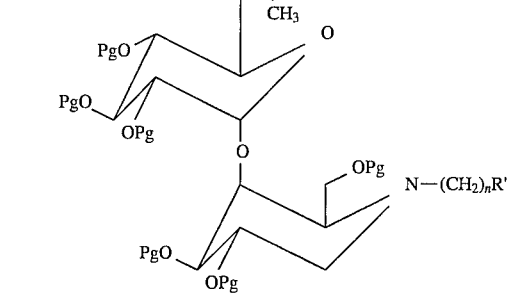  VI followed by the removal of any hydroxy-protecting groups and, if necessary, neutralizing any ammonium salts, and (b) condensing a compound of the formula

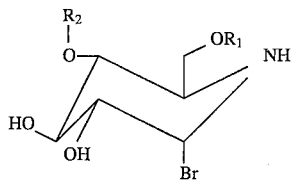  VII wherein one of $R_1$ and $R_2$ is H and the other is an α-D-glucopyranosyl moiety with a compound of the formula $X\text{-}(CH_2)_n R$ wherein X is bromo, n is zero, one or two, and R is as defined for Formula II, said reactions (a) and (b) producing compounds of the formula

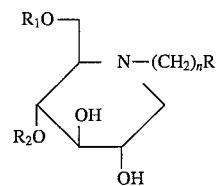  I wherein R, $R_1$, $R_2$ and n are as defined in Formula II, and optionally converting said compounds to their pharmaceutically acceptable salts.

* * * * *